United States Patent [19]

Athanasiou et al.

[11] Patent Number: 5,673,708
[45] Date of Patent: Oct. 7, 1997

[54] ARTICULAR CARTILAGE EVALUATOR AND METHOD FOR USING THE SAME

[75] Inventors: Kyriacos A. Athanasiou; George Constantinides; Dan R. Lanctot, all of San Antonio, Tex.

[73] Assignee: Board of Regents, The University of Texas System, Austin, Tex.

[21] Appl. No.: 427,058

[22] Filed: Apr. 24, 1995

Related U.S. Application Data

[63] Continuation-in-part of Ser. No. 231,612, Apr. 22, 1994, Pat. No. 5,503,162, and a continuation-in-part of Ser. No. 113,729, Aug. 27, 1993, Pat. No. 5,433,215, which is a continuation of Ser. No. 871,523, Apr. 21, 1992, abandoned.

[51] Int. Cl.$^6$ .................................................. A61B 5/10
[52] U.S. Cl. .................................................. 128/774
[58] Field of Search .................................. 128/737, 739, 128/740, 744, 774, 782; 73/81, 82, 85, 87, 573, 781, 855; 364/413.02, 505, 506, 508, 512

[56] References Cited

U.S. PATENT DOCUMENTS

| | | | |
|---|---|---|---|
| 4,132,224 | 1/1979 | Randolph | 73/81 |
| 4,159,640 | 7/1979 | Leveque et al. | 73/81 |
| 4,253,467 | 3/1981 | Frazier | 128/630 |
| 4,364,399 | 12/1982 | Dashefsky | 128/774 |
| 4,414,962 | 11/1983 | Carson | 128/6 |
| 4,461,281 | 7/1984 | Carson . | |
| 4,503,865 | 3/1985 | Shishido | 128/774 |
| 4,756,304 | 7/1988 | Watanabe | 128/6 |
| 4,764,114 | 8/1988 | Jeffcoat et al. | 128/776 |
| 4,848,141 | 7/1989 | Oliver et al. | 73/81 |
| 4,888,490 | 12/1989 | Bass et al. | 250/561 |
| 4,896,339 | 1/1990 | Fukumoto | 73/81 |
| 5,003,982 | 4/1991 | Halperin . | |
| 5,067,346 | 11/1991 | Field | 73/81 |
| 5,146,779 | 9/1992 | Sugimoto et al. | 73/81 |
| 5,494,045 | 2/1996 | Kiviranta et al. | 128/774 |

OTHER PUBLICATIONS

Mow, V.C. et al., "Biphasic Indentation of Articular Cartilage—II. A Numerical Algorithm and an Experimental Study," *J. Biomech.*, (1989) 22:853–861.

Mow, V.C. et al., "Biphasic Creep and Stress Relaxation of Articular Cartilage in Compression: Theory and Experiments," *J. Biom.* (1980) 102:73–83.

*Primary Examiner*—Max Hindenburg
*Attorney, Agent, or Firm*—Greenlee, Winner & Sullivan, P.C.

[57] ABSTRACT

An articular cartilage evaluator for determining the Index of Structural Integrity of articular cartilage. This computer-based system measures deformation or reaction force of articular cartilage through closed loop control of a testing tip and allows the measurement of peak force, stress relaxation behavior or creep behavior in vivo and in situ. This evaluator also allows the calculation of the tissue's material properties. A calibrator is also provided for calibrating the evaluator and attaching and removing a replaceable tip assembly.

35 Claims, 21 Drawing Sheets

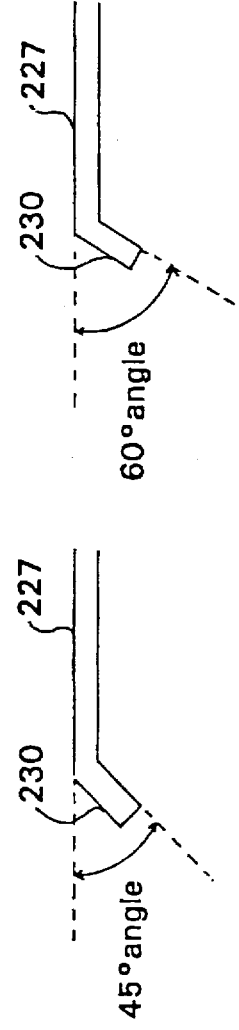
FIG. 27A
FIG. 27B
FIG. 27C
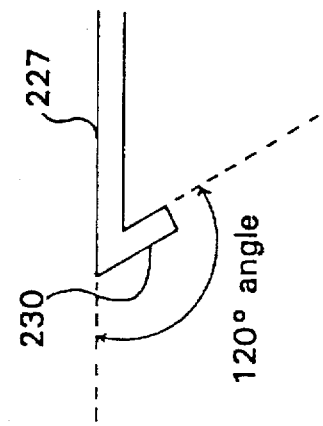
FIG. 27D
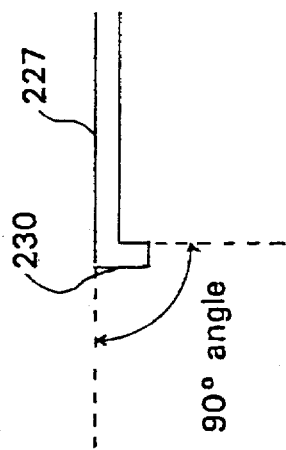
FIG. 27E

ARTICULAR CARTILAGE EVALUATOR AND METHOD FOR USING THE SAME

CROSS-REFERENCE TO RELATED APPLICATIONS

This application is a continuation-in-part of U.S. Ser. No. 08/231,612 filed Apr. 22, 1994, now U.S. Pat. No. 5,503,162 a continuation-in-part of U.S. patent application Ser. No. 08/113,729 filed Aug. 27, 1993, now U.S. Pat. No. 5,433,215 which is a continuation of U.S. patent application Ser. No. 07/871,523 filed Apr. 21, 1992, now abandoned, said applications being incorporated herein by reference.

FIELD OF THE INVENTION

The present invention relates to a system for measuring mechanical properties of articular cartilage in general and, more particularly, to an apparatus and method for defining and measuring the structural integrity of articular cartilage.

DESCRIPTION OF THE RELEVANT ART

The effects of articular cartilage degenerative diseases (such as osteoarthritis or *chondromalacia patella*) are visible to the naked eye when the disease has reached an advanced stage. Manifestations of these diseases include changes in the tissue's: 1) material properties (stiffness, permeability, compressibility), 2) biochemical composition (type II collagen, proteoglycan macromolecules, interstitial water content), and 3) morphological characteristics (surface fibrillation and fraying, osteophyte formation). At the early stages of articular cartilage degeneration, the tissue's stiffness decreases and its compressibility and permeability increase. Thus, a reliable means to quantify the initial stages of articular cartilage degeneration is to obtain its mechanical (or material) properties or characteristics. This can be accomplished during arthroscopy, which is an in vivo and in situ procedure, using a probe to examine qualitatively the articular surfaces. Using direct vision provided by an arthroscopic fiberoptic tube connected to a videocamera, the probe is used to palpate the tissue and, based on the tissue's deformation, the orthopaedist decides on the existence or severity of the disease. During this procedure, the orthopaedist also examines visually the surface characteristics of articular cartilage. This procedure is neither objective nor successful in determining the early stages of degenerative diseases, during which visual abnormalities are not present.

A device used to measure the "deformation resistance" of tissue, and particularly the articular surface of the patella, is described in U.S. Pat. No. 4,364,399. This arthroscopic instrument simply measures the amount of resistance pressure exerted by the cartilage at a given indentation. Positioning of the probe is manually accomplished, and perpendicularity of the probe relative to the cartilage surface is subjectively determined. The distance of indentation is mechanically calculated often using manual placement of the pressure transducer against the cartilage surface. A manual indentation process (as opposed to one which is computer-controlled) is not sufficiently accurate to allow repeatable, objective measurements. Manual indentation devices cannot programmably vary the applied indentations or forces in order to more accurately obtain material properties of the cartilage. This patented device does not measure the thickness of articular cartilage. Two tissues with the same material properties but unequal thicknesses will exhibit different deformation or force resistance. Thus, the thickness of the tissue must also be measured and used to normalize the measured tissue deformation or force resistance. Furthermore, the device of U.S. Pat. No. 4,364,399 is used to apply indentations onto cartilage without immobilizing the cartilage's subchondral bone relative to the device. Thus, under indentation, not only cartilage but other surrounding or underlying soft tissues deform. As a result, when both the cartilage and surrounding tissue deform, the applied cartilage indentation is not accurately known, and the measured cartilage resistance may be irrelevant. Thus, manual indentation devices provide an extremely subjective value of the tissue's deformation and force behaviors.

While indentation techniques are preferable over arthroscopic observations, manual indentation techniques which are not computer-controlled do not provide sufficient data to allow accurate and repeatable mechanical measurements to be taken of the cartilage.

SUMMARY OF THE INVENTION

The problems outlined above are in large part solved by the apparatuses and methods of the present invention. That is, the articular cartilage evaluators hereof can, in preferred embodiments, utilize high resolution displacements or loading forces placed substantially perpendicular upon the cartilage via a testing tip. Specifically, applied or resistive forces and applied or developing displacements are measured, recorded, and fed back upon the testing tip using a closed-loop computer feedback system. The computer-controlled evaluators with feedback of this invention can more accurately and repeatably measure the material properties of articular cartilage than prior art devices using stress relaxation and/or creep deformation techniques described below.

The evaluators of this invention allow the physician to measure force versus time profiles of cartilage, enabling calculation of the material properties of cartilage including stress relaxation and creep deformation as well as peak force and Index of Structural Integrity in vivo in the physician's office through small incisions, or during open joint surgery. The devices may also be used for in vitro tissue evaluation.

In one embodiment, the present invention contemplates an articular cartilage evaluator for measuring the creep deformation profile and/or the stress relaxation profile of cartilage, preferably articular cartilage. Creep deformation is the deformation of the cartilage as a function of time in response to a constant force or load placed upon the cartilage. Stress relaxation is the resistive force exerted by the cartilage over time in response to a set displacement.

The method for measuring "creep deformation" is a method in which a constant force is applied to the cartilage surface via a testing tip and resulting cartilage displacement under the tip is measured as a function of time. The constant applied force, the ensuing displacement profile and the tissue thickness can then be used to compute material properties of the cartilage. In addition, "stress relaxation" is defined as the technique by which a constant displacement distance is applied to the tissue via the evaluator and resulting force profile is measured. The constant applied displacement, the corresponding force resistance profile and the cartilage thickness can also be used to compute the material properties of the cartilage. Either creep deformation or stress relaxation techniques can produce an accurate measure of the material properties of the cartilage such as compressive stiffness, apparent compressibility, and permeability. Stiffness, compressibility and permeability are three important factors used in predicting the location and amount of the degenerative disease existing in articular cartilage.

The articular cartilage evaluators of this invention are devices for measuring force versus time profiles of cartilage based on the response of cartilage, preferably articular cartilage, to indentation comprising:

(a) a loading system comprising a testing tip for placement proximate to and for indenting the cartilage during use;

(b) an alignment system adapted to align the testing tip substantially perpendicular to the cartilage during use; and (c) a system for measuring the response of the cartilage to a force applied thereto by the testing tip during use, the force being applied to displace a portion of the cartilage during use; or (d) a system for measuring the response of the cartilage to a displacement applied thereto by the testing tip during use, the displacement being applied to create a resistive force in the cartilage during use.

The loading system comprises any system known to the art for exerting force, referred to as "loading" herein, including manually-exerted force, or a computer-controlled actuator such as a motor, which moves a shaft which may be directly attached to the testing tip, or in the hand-held embodiment hereof, includes a loading force translation system for changing the direction and speed of the motion imparted by the motor shaft to the testing tip. The loading system also includes a system for controlling the amount of force exerted against the cartilage, preferably articular cartilage, by the testing tip, such as a computer-controlled feedback mechanism as described herein, or other systems known to the art.

The alignment system may comprise a reflected light system as described hereinafter, a perpendicularity rim as described with respect to a hand-held embodiment of this invention, piezo electric films disposed on a rim acting as pressure-sensitive force transducers, or other systems known to the art such as circular or non-circular flanges at the distal end of the device.

The system for measuring the response of the cartilage to the force applied may comprise any system known to the art including position detectors, force transducers, and combinations thereof, and also including computerized data collection, calculation and display components.

The apparatus includes a loading system comprising a loading shaft having a proximal end and a distal end. The distal end is a testing tip which can be placed proximate to cartilage to be measured. The term "distal" is used with respect to the operator, the "distal" end of the device being the end closest to the patient. An electromechanical actuator capable of axially moving the shaft in response to electrical input is attached to or near the proximal end of the shaft. The actuator may include a motor and a cam used to axially displace the distal end at a constant force upon the cartilage. A system is provided to measure the response of the cartilage, preferably articular cartilage, to force applied thereto. To measure creep deformation, a computer is used to programmably command the motor to apply constant force and it also records the amount by which the distal end displaces the cartilage while maintaining constant force upon the cartilage. Alternatively, to measure stress relaxation the computer commands the motor to measurably force the distal end to a set displacement upon the cartilage. The computer also records the resistive force exerted by the cartilage upon the distal end at the set displacement distance.

The apparatus comprises means for closed-loop controlling creep deformation and stress relaxation tests performed on cartilage. The apparatus includes a loading system having a proximal end and a distal end, wherein a testing tip at the distal end is placed substantially perpendicular to or near cartilage to be measured. A motor may be attached to the proximal end to extend the distal end upon the cartilage, and a computer is adapted to monitor force and displacement readings of said cartilage by actuating the motor a set distance or a set force in accordance with a closed-loop-controlled input sent from the proximal end to the computer.

According to one aspect of the apparatus for closed-loop controlling creep deformation and stress relaxation, a force transducer is attached to or included within the loading system to measure force applied to the cartilage by the testing tip or the resistive force applied by cartilage against the testing tip. A position detector is also coupled to the loading system to measure the distance by which the testing tip extends upon the cartilage. The computer operates on a closed loop principle by receiving input from the force transducer and position detector, and then outputting programmed electrical signals to the motor in accordance with the input.

The present invention also contemplates methods and systems for determining substantially perpendicular placement of a loading shaft upon the outer surface of the cartilage comprising a perpendicularity rim at the distal end of the device.

The present invention also contemplates a method for determining material properties of cartilage, preferably articular cartilage. The method includes positioning the testing tip at the distal end of the device through skin substantially perpendicular to underlying cartilage. The distal end is then measurably extended upon said cartilage at a measurable force, wherein material properties and peak force can be calculated from measuring the force and the distance by which the testing tip extends into the cartilage.

The invention also comprises a computer adapted to calculate the Index of Structural Integrity (ISI) of the cartilage, preferably articular cartilage, as an indication of the health of the cartilage. The ISI is calculated based on the force versus time profile exhibited by the cartilage at a set displacement.

The invention provides a hand-held device wherein the testing component may be hand-held by the physician during use to measure the salient material properties of cartilage, preferably articular cartilage, in situ and in vivo. This embodiment, termed the "Articular Cartilage Evaluator" or "ACE" herein comprises a handle, preferably between about 5 mm and about 40 mm in diameter, and a head for insertion through the skin between about 2 mm and about 10 mm in diameter, with a testing tip having a diameter of less than about 2 mm, preferably about 0.5 mm.

The device may be used to measure stress relaxation of articular cartilage, maximum force required to displace the cartilage a predetermined distance, and force required to maintain said displacement after the cartilage has reached equilibrium. These measurements are performed within ten seconds or less, preferably within about 1 second or less. In a preferred embodiment, measured data are used to compute and express, preferably by means of display, a value indicating the relative health of the tissue. Preferably this value is a ratio termed herein the "Index of Structural Integrity" or "ISI." This index is a number from one to ten wherein ten represents healthy tissue and one represents severely degenerated tissue. The value is derived from measured properties of the cartilage compared to a database comprising values for cartilage having known states of health. Preferably the database comprises mean values for the measured properties of healthy tissue of the same type as that being evaluated. "Tissue of the same type" means tissue taken from the same location in the body, e.g. when tissue from the central portion of the anterior aspect of the medial femoral condyle is being evaluated, it is compared with corresponding measurements for healthy tissue from the central, anterior medial femoral condyle in the database, preferably with mean measurements for several, e.g. at least about twelve of such measurements for healthy tissue. Preferably the measurement for healthy tissue is assigned a value of ten and the ratio is expressed as an integer from one to ten (the ISI).

The ACE comprises a loading system terminating in a testing tip for placement proximate to, and for indenting the cartilage during use. The ACE consists of a hand-held component comprising a handle portion and a shorter portion or head at an angle thereto between about 30° and about 180°, preferably about 90°. The handle portion contains a motor operatively connected to a motor shaft whereby the motor produces horizontal (axial) motion in the motor shaft during use. The head is inserted through the patient's skin to contact the cartilage to be tested and comprises a force translation system for changing the direction and speed of motion imparted by the motor shaft, said force translation system comprising a slider attached to the distal end of the motor shaft engaged within a slide disposed within the head at an angle such that when the slider moves forward on the slide, the slide pushes down against a loading wedge beneath it, which in turn pushes down against a force transducer, the probe at the distal end of which pushes against the testing tip of the device. The testing tip at the distal end of the head is used to indent the cartilage. Preferably, the amount of horizontal motion by the motor shaft is translated to a lesser amount of motion of the testing tip. The loading system, comprising the foregoing components involved in exerting and translating force from the motor to the testing tip, thus causes the testing tip which is placed distal to the loading wedge, to move against and displace a portion of the cartilage tissue.

The hand-held portion of the device also comprises a position detector to measure the distance travelled by the motor shaft or the testing tip, preferably the motor shaft, in response to actuation by the motor. Preferably the position detector comprises an optical encoder having a displacement resolution of about 0.1 μm.

The force transducer is adapted to provide data to determine the force applied by the testing tip to the cartilage over time. The force transducer is preferably placed between the loading wedge and the testing tip and comprises a surface placed in pressure communication with the loading wedge. Examples of force transducers include strain gauge based transducers and piezo electric transducers.

The hand-held portion of the ACE is connected to a computer programmed to measure and control the movement of the testing tip over time in response to data from the force transducer or position detector or both.

The distal end of the hand-held component of the ACE comprises an alignment system for aligning the testing tip substantially perpendicular to an outer surface of the cartilage during use. The outer sheath of the head of this component may be equipped with a perpendicularity rim for placing adjacent to the surface of the cartilage during use which serves as an alignment system for the testing tip. Alternatively, the distal end of the sheath is adapted to receive a replaceable tip assembly which includes a perpendicularity rim for placing against the surface of the cartilage.

The ACE is adapted to measure stress relaxation and creep deformation. These data can then be used to calculate the material properties of articular cartilage or the Index of Structural Integrity (ISI). Because of the small size of the ACE and the extremely small depth of indentation required compared to cartilage thickness at the test site, the thickness of the cartilage need not be measured in order to calculate the material properties and/or the ISI. The ACE also may be used to display the Index of Structural Integrity as an aid to orthopaedic diagnosis of the cartilage.

The system for evaluating cartilage of this invention also includes a calibrator for use with the ACE. Preferably designed for one-time use, the calibrator is a box containing a sterile replaceable tip assembly and a calibration pad having a known stiffness. The calibrator also comprises means for attaching and removing a replaceable tip assembly on the evaluator. The operator inserts the head end of the ACE indenter into a slot in the calibrator where it is positioned for attachment of the replaceable tip assembly. The operator exerts pressure from beneath on a platform holding the replaceable tip assembly which then snaps into place on the head of the ACE. The operator then moves the head of the ACE further into the interior where it is positioned over a calibration pad having a known stiffness. The ACE is activated and from the reading taken from the calibration pad, the computer recalibrates the device. After the ACE has been used to test a patient's cartilage, it may be re-inserted into another slot in the calibrator having separate channels for receiving the head and rim of the indenter whereby the replaceable tip assembly is wedged apart from the rest of the head when the channels diverge.

An improved hand-held indenter comprises a disposable distal end and a reusable proximal end containing the motor. This eliminates a number of sterilization problems. This improved embodiment, called the Actaeon™ indenter herein, also comprises means for standardizing the amount of force communicated to the distal end of the evaluator as a result of the operator activating the evaluator. Ordinarily, when the activation switch is depressed, a torque is produced which is transmitted to the cartilage as a placement force exerted by the perpendicularity rim against the cartilage. The means for standardizing this force comprise a thumb trigger switch designed to avoid influencing the peak force measurement by the amount of force the operator applies to the handle when depressing the switch. To make this force consistent, the torque produced on the handle must be consistent. The thumb trigger switch standardizes the amount of force applied to the switch by allowing the cartilage indenter to operate only if a predetermined force has been applied to the switch. Further, the handle of the Actaeon™ incorporates a pistol-type grip which encourages the operator to hold the indenter the same way for each test, thus providing a means for producing a repeatable torque on the handle which also helps create a standardized, consistent placement force against the cartilage.

To seal the connection between the disposable and reusable portion of the Actaeon™, a roll-out prophylactic membrane is stretched across the interface. The seal is initially on the disposable portion. Then after the reusable motor assembly is coupled to the disposable portion, the seal is rolled out over the connection.

The connections between the disposable and reusable sections are made via small electrical contacts designed so that electrical contact is made when the reusable motor assembly, which is connected to the data cable, is connected to the disposable section.

Disposable sections for the Actaeon™ are made with an assortment of head angles between about 30° and about 180°. These different angles allow the Actaeon™ to test cartilage surfaces that may not be accessible with the standard 90° head. The evaluator comprises electrical means for informing the computer of the head angle and for compensating for the head angle in calculating the force exerted by the cartilage against the testing tip. The computer can identify the head angle being used by means of feedback from the electrical contacts and compensate by recalculating the ISI based on the ratio between the force exerted by the shaft and the force translated to the cartilage by the loading wedge.

The computer for the Actaeon™ is comprised in a controller containing a rechargeable battery, an intelligent charger, a motor driver, an interconnecting custom-made circuit board and signal conditioner, and using a computer with an EEPROM (electrically erasable permanent read-only memory), so that the system is completely portable. The program used to run the probe is downloaded and permanently resides on the EEPROM. An LCD (liquid crystal display) shows the measured force. The intelligent charger is used to selectively charge the battery when the controller is connected to a 110 volt AC external supply. A circuit is used to determine when the battery needs to be charged. After recharging, it automatically cuts external power to the charger unit.

Methods for determining the response of cartilage, preferably articular cartilage, to indentation are also provided herein comprising positioning a testing tip through skin substantially perpendicular to underlying cartilage, displacing a portion of the cartilage with the testing tip; and measuring the response of the cartilage. The response of the cartilage may be measured in terms of force exerted against the testing tip by the cartilage at a set displacement or displacement of the cartilage at a constant force applied by the testing tip. Preferably these measurements are compiled over time by a computer system and may be used to control the force exerted by the testing tip against the cartilage during the test and to calculate the properties of the cartilage.

BRIEF DESCRIPTION OF DRAWINGS

Other objects and advantages of the invention will become apparent upon reading the following detailed description and upon reference to the accompanying drawings in which:

FIG. 25 depicts the thumb trigger switch.

FIGS. 27A–E illustrate some of the head angles available.

Figure 1A:
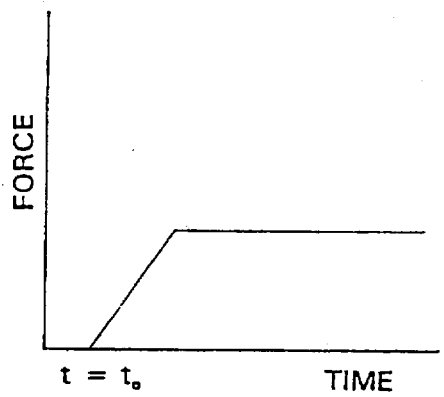
FIGS. 1A and 1B are graphs showing creep deformation at constant force achievable by the present invention.

While the invention is susceptible to various modifications and alternative forms, the specific embodiments thereof have been shown by way of example in the drawings and will herein be described in detail. It should be understood, however, that the drawings are not intended to limit the invention to the particular form disclosed, but on the contrary, the intention is to cover all modifications, equivalents and alternatives falling within the spirit and scope of the invention as defined by the appended claims.

DETAILED DESCRIPTION OF THE INVENTION

Figure 1B:
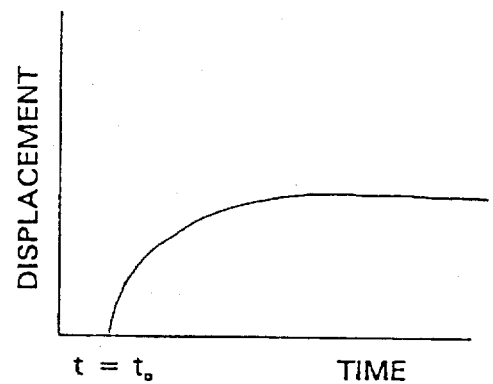

FIG. 1A is a graph illustrating the constant force applied by the indention tip. FIG. 1B shows a typical, corresponding, articular cartilage deformation profile as a function of time. Creep deformation is particularly suited for measuring the material properties, e.g. compressibility, stiffness and permeability, or the ISI of articular cartilage.

Figure 2A:
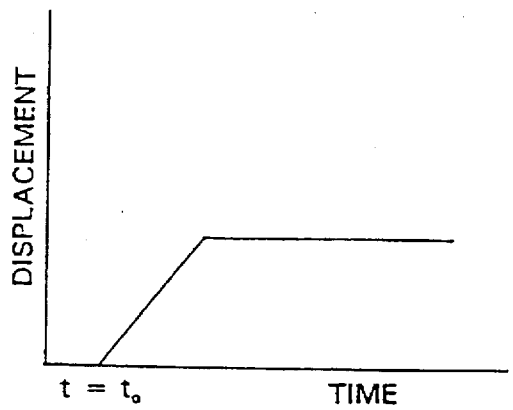
FIGS. 2A and 2B are graphs showing stress relaxation at constant displacement achievable by the present invention.
Figure 2B:
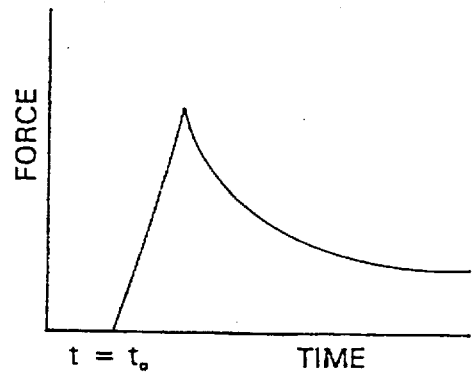

Similar to the creep deformation equilibrium measurement technique described above, stress relaxation equilibrium measurement utilizes the same apparatus while applying a different programmed technique. Instead of applying a constant force and measuring the resulting displacement, the stress relaxation technique applies a set displacement upon the testing tip and measures the resulting resistive force exerted by articular cartilage upon the testing tip as shown in FIGS. 2A and 2B.

Stress relaxation and creep deformation provide inputs by which material properties of articular cartilage can be obtained. Such properties include, but are not limited to, compressive stiffness, apparent compressibility and permeability. Permeability is the degree of difficulty of movement of articular cartilage interstitial fluid in and out of extracellular solid matrix or collagen material. Thus, articular cartilage evaluator 10 can be used as either a prognostic or diagnostic tool in orthopaedics by obtaining variations in material properties of articular cartilage in a joint. An orthopaedic physician can thereby use the present apparatus to identify areas with potential for degeneration. This information will help the physician suggest changes in physical activities and exercise, and design surgical strategies which can alleviate mechanical stresses in these subject areas. Thus, the process of degenerative disease may be curbed.

Any algorithm which utilizes stress relaxation and creep deformation data obtained hereinabove and then applies that data to obtain material properties, such as compressibility, stiffness and permeability, falls within the scope and spirit of this invention.

Figure 3A:
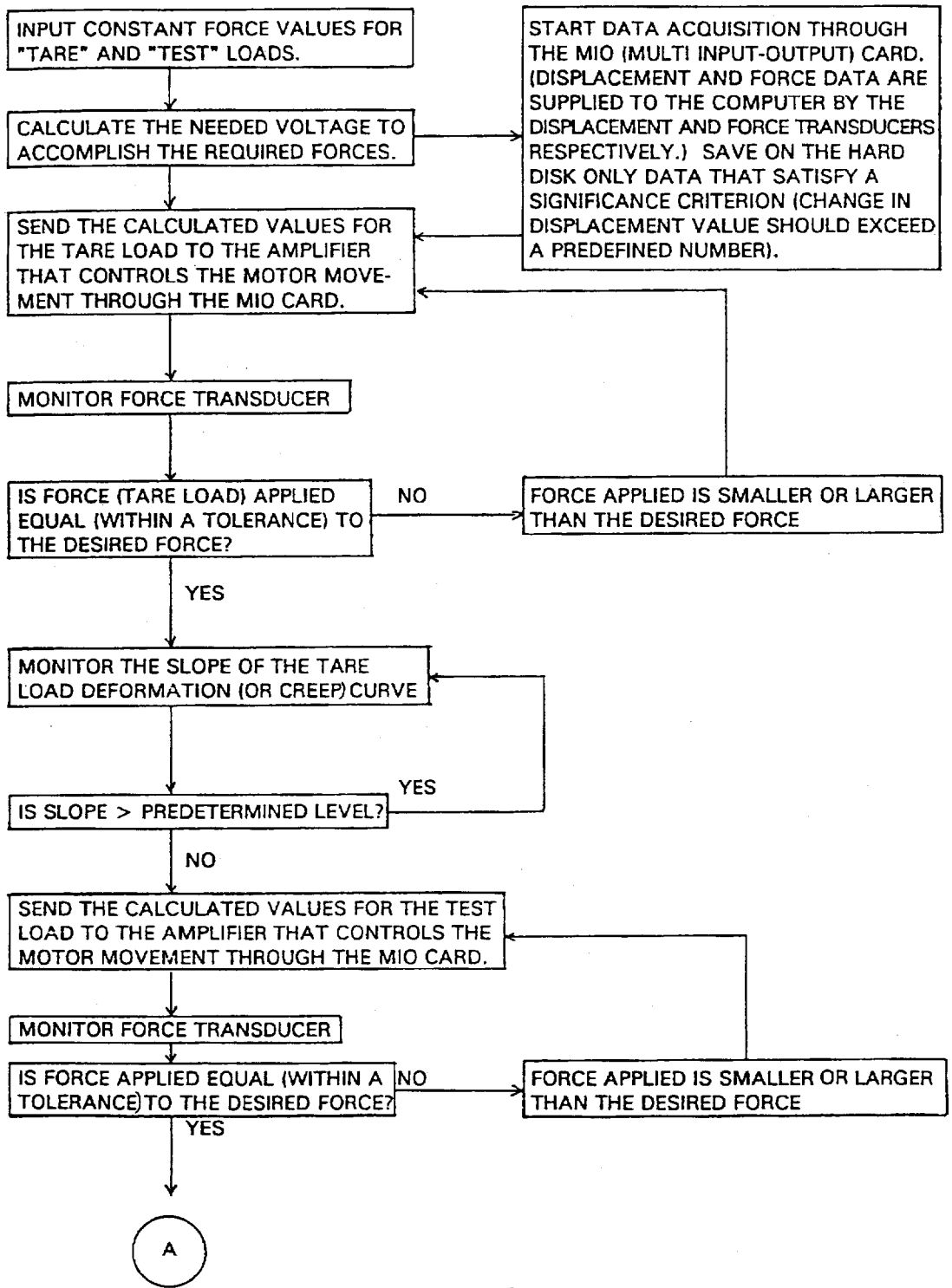
FIGS. 3A and 3B present a flow diagram of steps used to perform creep deformation achievable by the present invention.
Figure 3B:
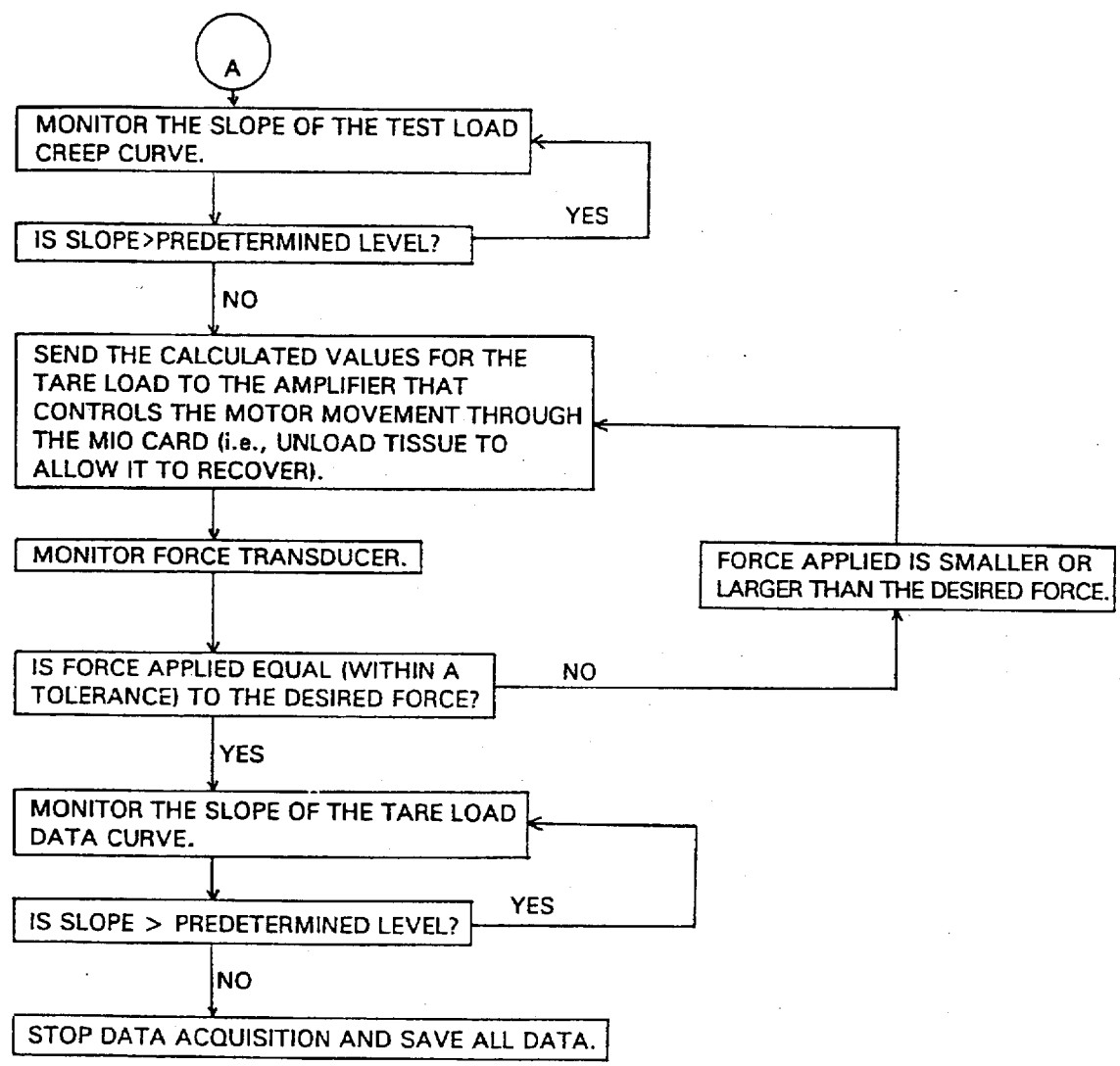
Figure 4A:
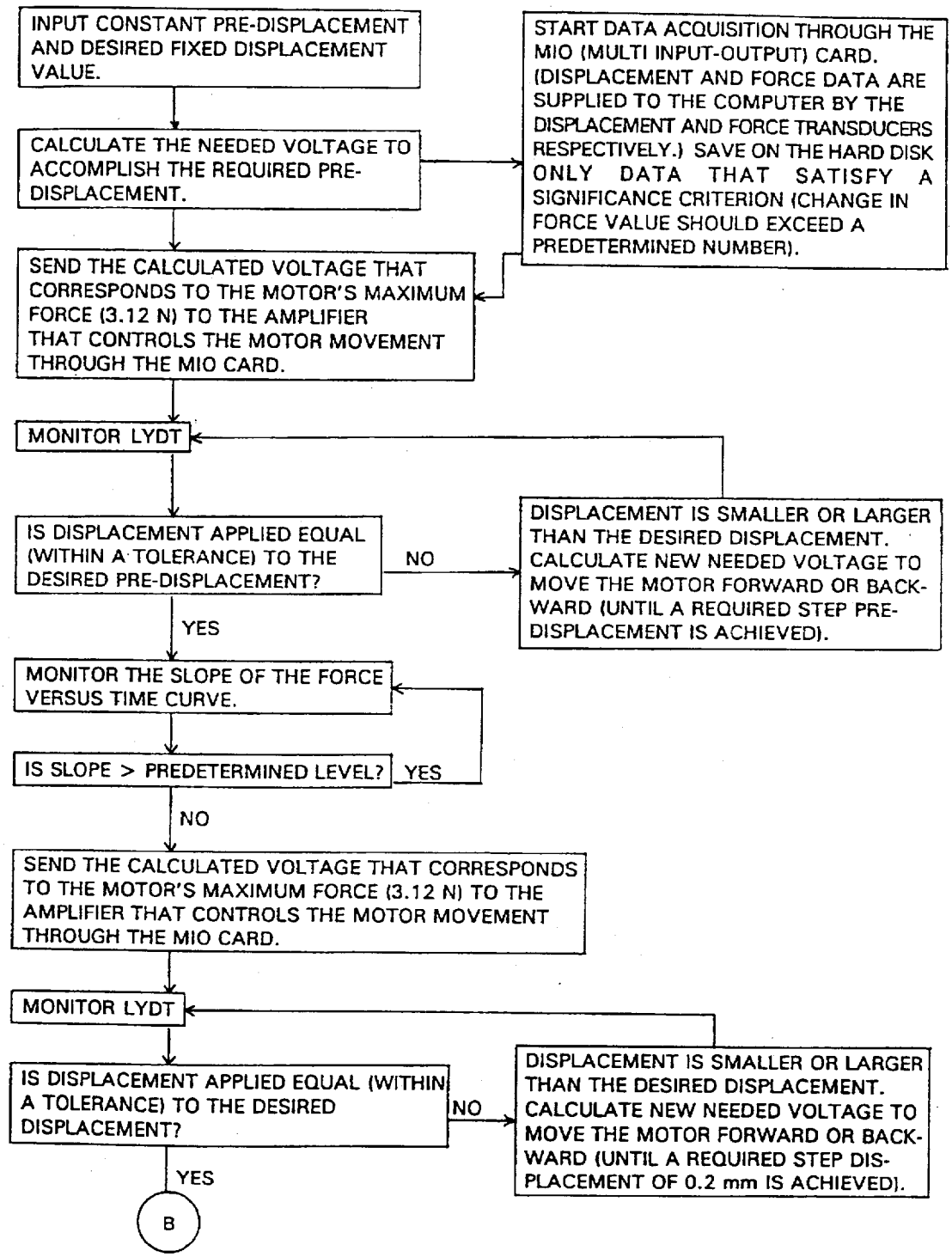
FIGS. 4A and 4B present a flow diagram of steps used to perform stress relaxation achievable by the present invention.
Figure 4B:
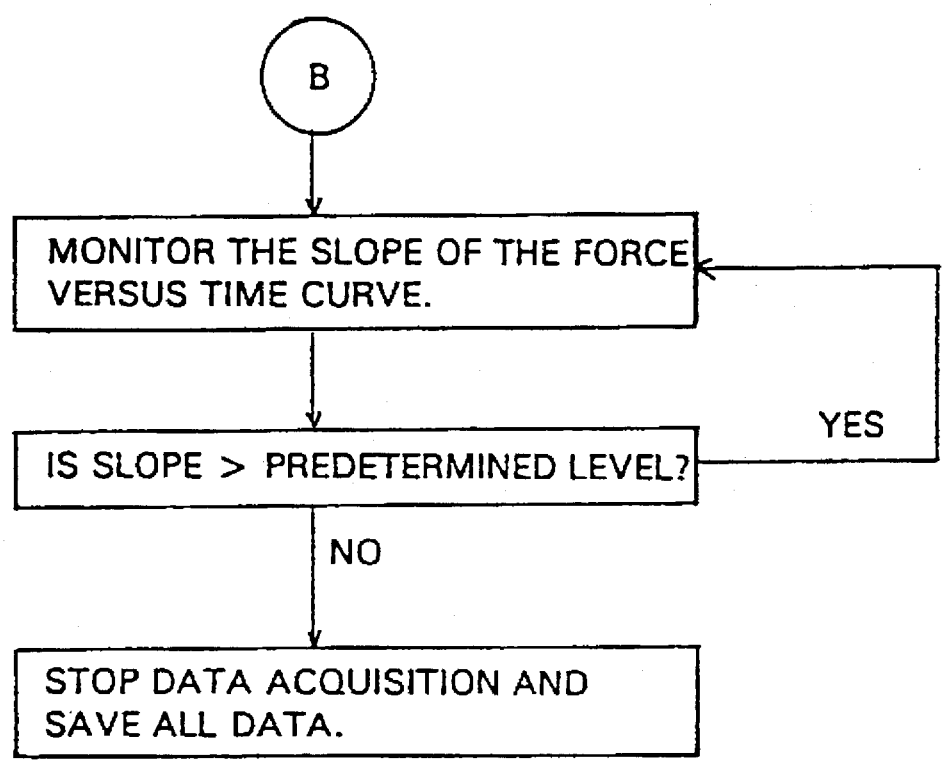

Flow diagrams of various programming steps, capable of being input into a computer and necessary to achieve creep deformation, stress relaxation and thickness measurements, are illustrated in FIGS. 3 and 4. Any suitable program language operable with the computer can be utilized to reconfigure the computer to achieve the necessary test steps.

As shown in FIG. 3, creep deformation includes numerous programmable steps beginning with both tare and test loads being input into the computer. The tare and test loads are constant force values which the computer will use to monitor deformational characteristics of articular cartilage. A multi-input/output (MIO) card associated with the computer controls and monitors both the tare and test loads and displacement applied to the testing tip of the present invention. The tare load is calculated in terms of voltage and sent to amplifier which then controls movement of the motor. The resulting force is monitored by a force transducer. If the applied tare load is substantially equal to the desired force or load, then the slope of the tare load deformation or tare creep curve is monitored. If the slope of the tare creep curve is less than a predetermined level, then test operations can begin.

Creep deformation testing begins after tare loads are applied. Specifically, testing begins by sending calculated values for the test load to an amplifier which then controls the motor. As stated above, tare load is generally less than test load and is used to initialize or set a bench mark for subsequent test readings. After the test load is applied via a motor, a force transducer will monitor the resulting force to determine if the force applied, or test load, is substantially equal to the desired force. If test load is substantially equal to desired force, then the slope of the test load creep curve is monitored to determine if the slope is less than a predetermined level. Once the slope drops below the predetermined level, data acquisition and control stops and the experiment is finished.

Throughout the creep deformation process, a closed-loop system allows close monitoring of resultant force upon the transducer and readjustment of applied force sent by the motor. The closed-loop system is controlled by programmed reconfiguration of the computer. The software program necessary to achieve reconfiguration resides on hard disk of computer 76 or it can be stored on a portable memory medium such as a floppy disk, CD ROM, electrically erasable permanent read only memory (EEPROM), etc.

FIG. 4 illustrates the programmable steps used in achieving stress relaxation measurements by the system of the present invention. Similar to creep deformation, stress relaxation can measure the behavior of articular cartilage in response to various displacement values exerted upon the articular cartilage. However, unlike the constant force values used in creep deformation, stress relaxation uses constant or fixed displacement values. In particular, stress relaxation requires a fixed displacement value be sent from the computer to the motor. The desired voltage needed to accomplish the required pre-displacement is calculated and also sent to the motor. If the resulting displacement is substantially equal to the desired pre-displacement, then the slope of the corresponding force versus time curve is measured. Once the slope falls below predetermined level, the motor's maximum force is applied and the resulting displacement is monitored. If the resulting displacement being applied to the testing tip is substantially equal to the desired displacement, then the slope of the force versus time curve is determined such that once the slope is less than a predetermined level, data acquisition is discontinued and all data is stored within the computer. Similar to creep deformation data, stress relaxation data can be saved and used immediately or at a later time.

Figure 5:
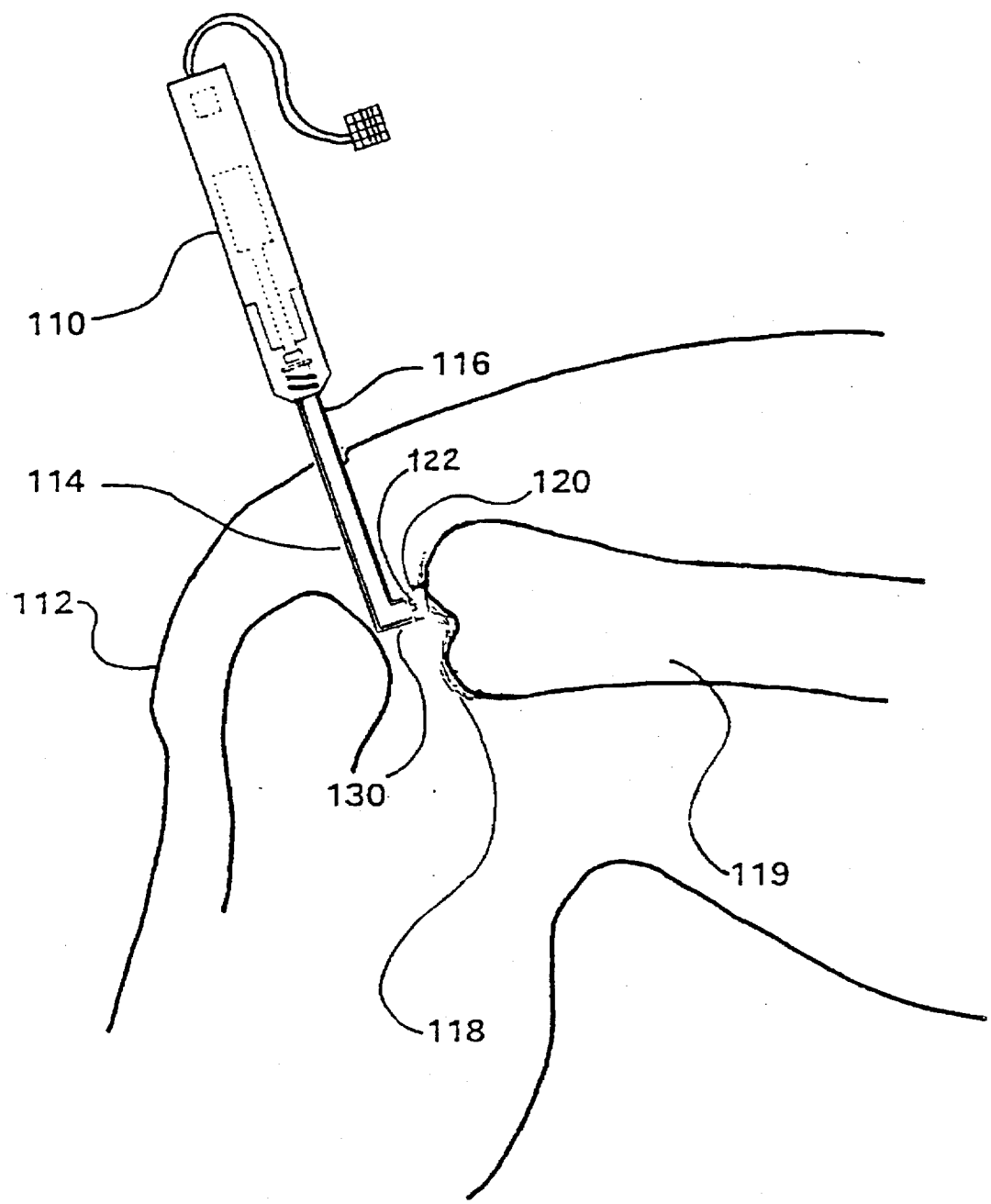
FIG. 5 depicts the hand-held articular cartilage evaluator (ACE), showing the device as used to measure properties of articular cartilage of the knee, showing the size of the ACE relative to the knee.

The hand-held testing component of this invention, called the articular cartilage evaluator (ACE) 110, is shown in FIG. 5. The hand-held portion of the ACE is preferably of a generally cylindrical shape. The distal end or head 130 of the component is shown penetrating a patient's knee 112 through a small surgical incision 116, preferably about a 5 mm incision, into the joint cavity 114. The ACE comprises an alignment system to ensure that the force by the ACE against the articular cartilage is exerted perpendicularly. This alignment system includes perpendicularity rim 120 on the distal end of the ACE in contact with the articular cartilage 118 overlying the tip of the femur 119. The termdistal is used with respect to the operator of the ACE, the handle being the proximal end and the end farthest from the operator being the distal end. After placement of the perpendicularity rim against the articular cartilage, testing tip 122 is moved to indent articular cartilage 118.

Figure 6:
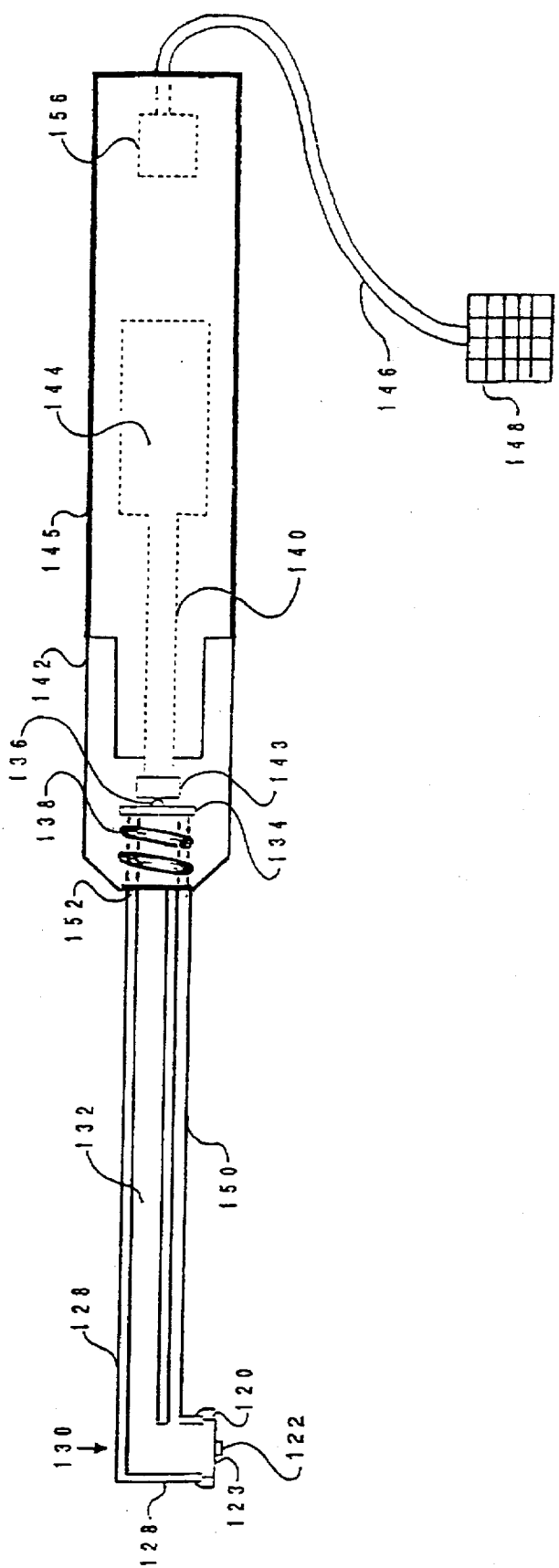
FIG. 6 depicts the hand-held component of the ACE in further detail.

FIG. 6 provides further details of the structure of the ACE. An electromechanical linear actuator, e.g. motor 144, preferably a DC encoder Mike Drive Model No. 18224, of Oriel Company, Stratford, Conn. having a maximum 22 pound force output and a resolution of 0.1 μm, in the handle of the ACE (the larger, proximal end of the device) is connected to motor shaft 140, the enlarged head of which rests against bearing 136, which is preferably a steel ball bearing, attached to the tip of linearly (axially) moving shaft 132. A contact-retaining spring 138 lies around linearly moving shaft 132 between fixed spring retainer 152 and movable spring retainer 134. Motor coupler 142 surrounds movable spring retainer 134 and is fixedly attached to the casing 145 of motor 144. Linearly moving shaft 132 is surrounded by sheath 128 which abuts fixed spring retainer 152. Sheath 128 may form an angle from about 30° to about 180° between its distal and proximal ends. The distal end of sheath 128 encloses head 130 and is preferably cylindrical in shape. Attached to the distal end of the head is perpendicularity rim 120 which forms a part of replaceable tip assembly 123.

Figure 8:
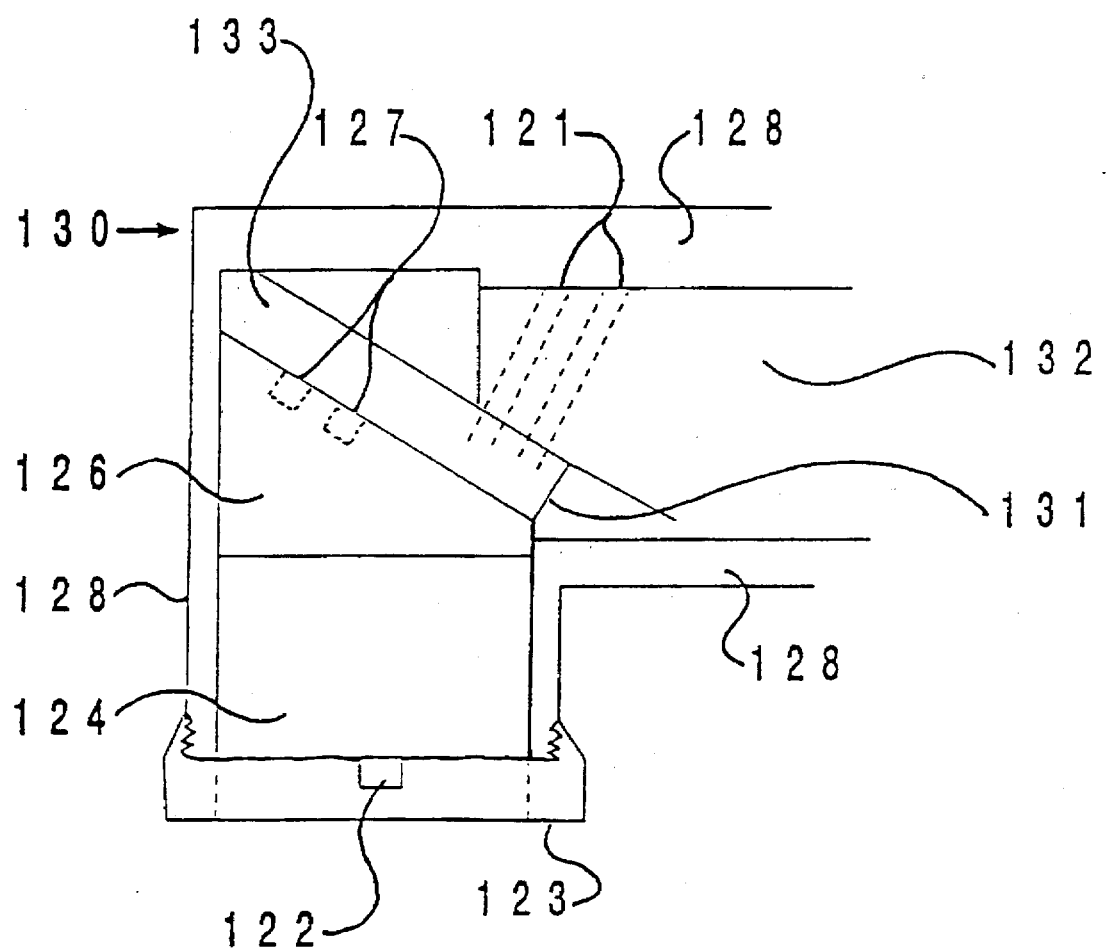
FIG. 8 depicts a side view of details of the head of the ACE.

The head is shown enlarged in FIG. 8. As shown in FIG. 8, linearly moving shaft 132 terminates at its distal end in a slider 131, which is connected to the distal end of linearly moving shaft 132, preferably using screws in slider screw holes 121. The underside of the distal end of shaft 132 slopes upward in the distal direction, preferably at an angle of about 30° for a head at a 90° angle from the handle. The slider 131 slidably engages with slide 133. Slide 133 abuts loading wedge 126. Force transducer 124, preferably force transducer Model ALD-SP-MICRO of A. L. Design, Buffalo, N.Y., is operatively connected, preferably glued, to loading wedge 126. Testing tip 122 is part of the replaceable tip assembly 123. The testing tip 122 is operatively connected to force transducer 124, preferably by means of screwing replaceable tip assembly 123 to the threaded distal end of the sheath 128 surrounding the head of ACE. The entire assembly, comprising slider 131, slide 133, loading wedge 126, force transducer 124, and testing tip 122, is encased in sheath 128 which is preferably of stainless steel. As the device operates to indent the cartilage, shaft 132 moves forward, slider 131 forces the slide 133 to move downward. Slide 133 in turn, forces the loading wedge 126 to move downward, which in turn forces the force transducer 124, to move downward and which in turn forces testing tip 122 to move downward. As the device operates to retract the testing tip 122 from the cartilage, shaft 131 moves backward, and slider 131 forces the slide 133 to move upward. Slide 133 in turn pulls loading wedge 126 upward which pulls force transducer 124 and attached testing tip 122 upward away from the cartilage.

In the embodiment depicted the head 130 is at an angular orientation of 90° with respect to the handle but this angle may vary from about 30° to about 180°. The head may be replaceable so that different heads of different orientations may be attached to the handle, or the angle of the head may be adjustable.

Figure 9:
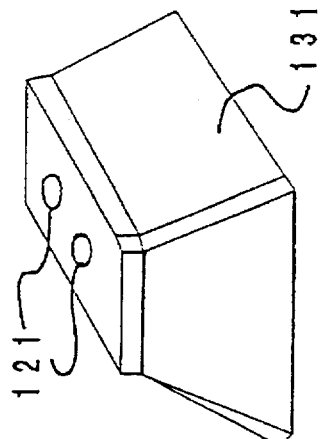
FIG. 9 is an enlarged side view of the loading wedge.

FIG. 9 is a side view of the loading wedge 126 showing wedge screw holes 127 and machine groove 129 for the force transducer excitation and signal wires. Preferably the loading wedge 126 has four symmetrical screw holes 127 and is attached to slide 133 using four screws. The acute angle of loading wedge 126 is preferably about 30° for a 90° head.

Figure 10:
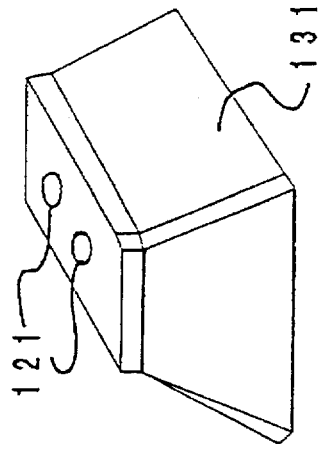
FIG. 10 is an enlarged three-dimensional view of the slider.
Figure 12:
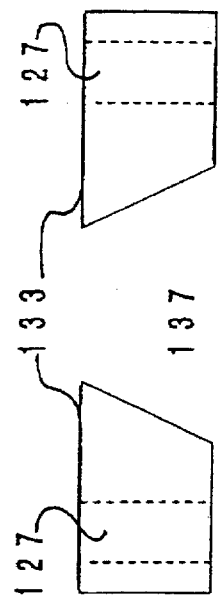
FIG. 12 is a front view of both halves of the slide.
Figure 11:
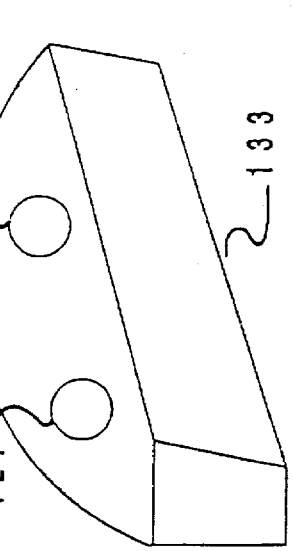
FIG. 11 is an enlarged three-dimensional view of one-half of the slide.
Figure 13:
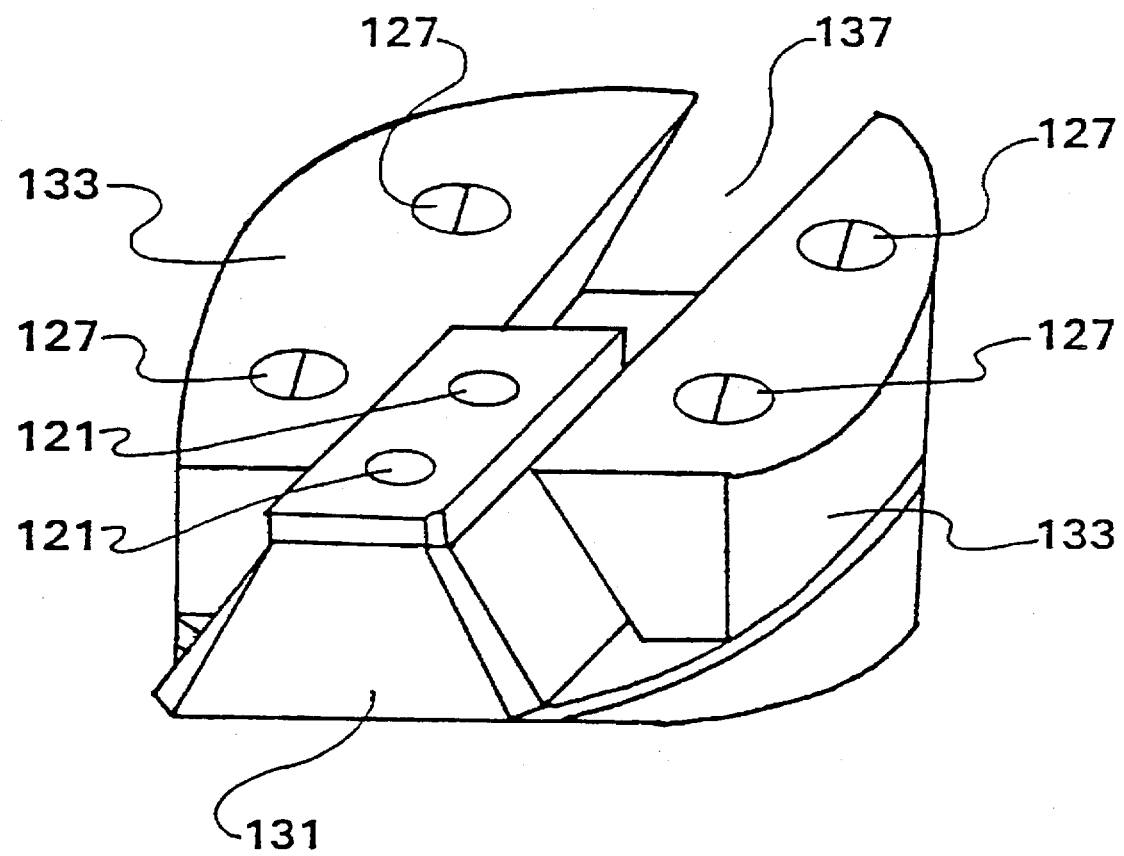
FIG. 13 is a three-dimensional view of the slide engaged with the slider.

FIG. 10 is a three-dimensional view of slider 131 showing slider screw holes 121, which are an extension of the slider screw holes 121 shown in FIG. 8, and adapted to receive screws connecting slider 131 to the distal end of shaft 132. Slider is preferably shaped like a truncated tetrahedron. Slide one-half of which is shown in three dimensions in FIG. 11, is connected to loading wedge 126 by screws extending into wedge screw holes 127 which extend into wedge 126 as shown in FIG. 9. FIG. 12 shows both halves of slide 133 from a viewpoint at the front end of the ACE looking downward in the direction of the long axis of slide 133. The two halves of slide 133 are attached to loading wedge 126 using screws extending into wedge screwholes 127 so as to form a slide channel 137 adapted to receive slider 131. FIG. 13 shows slider 131 engaged with slider 133 such that slider 131 is able to move in groove 137 between the two halves of slider 133.

Figure 14:
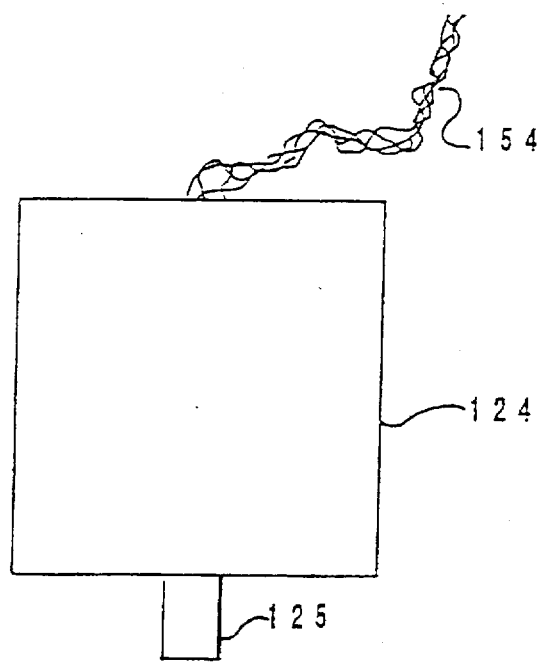
FIG. 14 is an enlarged side view of the force transducer.

FIG. 14 is an enlarged view of force transducer 124 showing force transducer excitation and signal wires 154 (which lead to fast connector 148 shown in FIG. 6) and force transducer probe 125.

Figure 15:
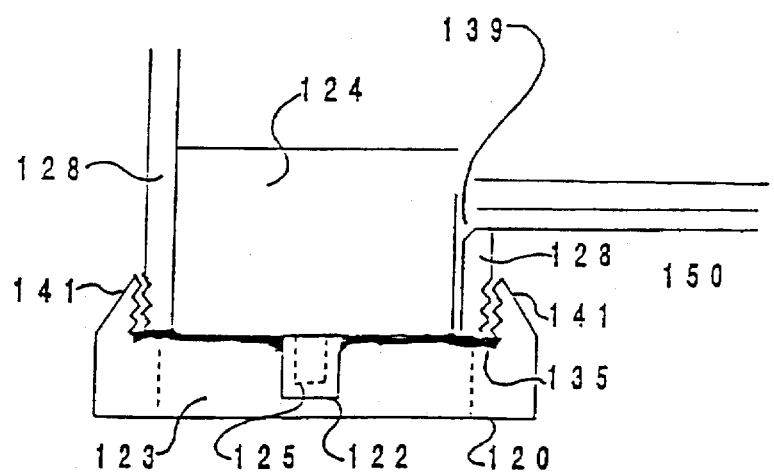
FIG. 15 is an enlarged side view of the distal portion of the head equipped with a replaceable tip assembly.

FIG. 15 depicts the distal portion of the ACE including replaceable tip assembly 123 comprising perpendicularity rim having screw-threaded lips 141 adapted to screw onto the threaded distal end of sheath 128, and membrane 135, preferably a silicone rubber or latex membrane, attached e.g. by gluing to the proximal end of perpendicularity rim 120. Testing tip 122 has a recess into which force transducer probe 125 fits. The bottom, or distal surface of replaceable tip assembly 123 is a circle having an open center formed by perpendicularity rim 120. The bottom surface of perpendicularity rim 120 may be smooth or knurled. Also shown in FIG. 15 is pocket 139 for force transducer excitation and signal wires (not shown) formed in the end of transducer excitation and signal wire tube 150 which runs along the bottom of the proximal (or horizontal) portion of sheath 128. Sheath 128 is perforated and indented to accommodate pocket and transducer excitation and signal wire tube 150. The force transducer excitation and signal wires lead from force transducer 124 to pocket 139, into transducer excitation and signal wire tube 150.

As shown in FIG. 6, the proximal end of the ACE is connected via data cable 146 to fast connector 148. Four force transducer excitation and signal wires 154 (best seen in FIG. 14) run from force transducer 124 along the underside of sheath 128 enclosed in transducer excitation and signal wire tube 150. These force transducer excitation and signal wires 154 run into the space inside motor coupler 142 and preferably through motor casing 145 to data cable 146, and thence to fast connector 148. Position detector data wires (not shown) from position detector 156, which is preferably an optical encoder built into the motor, also run into data cable 146. Data cable 146 contains a total of ten wires; four force transducer excitation and signal wires 154 (FIG. 14), three position detector data wires (not shown), and three motor controller wires (not shown).

Figure 7:
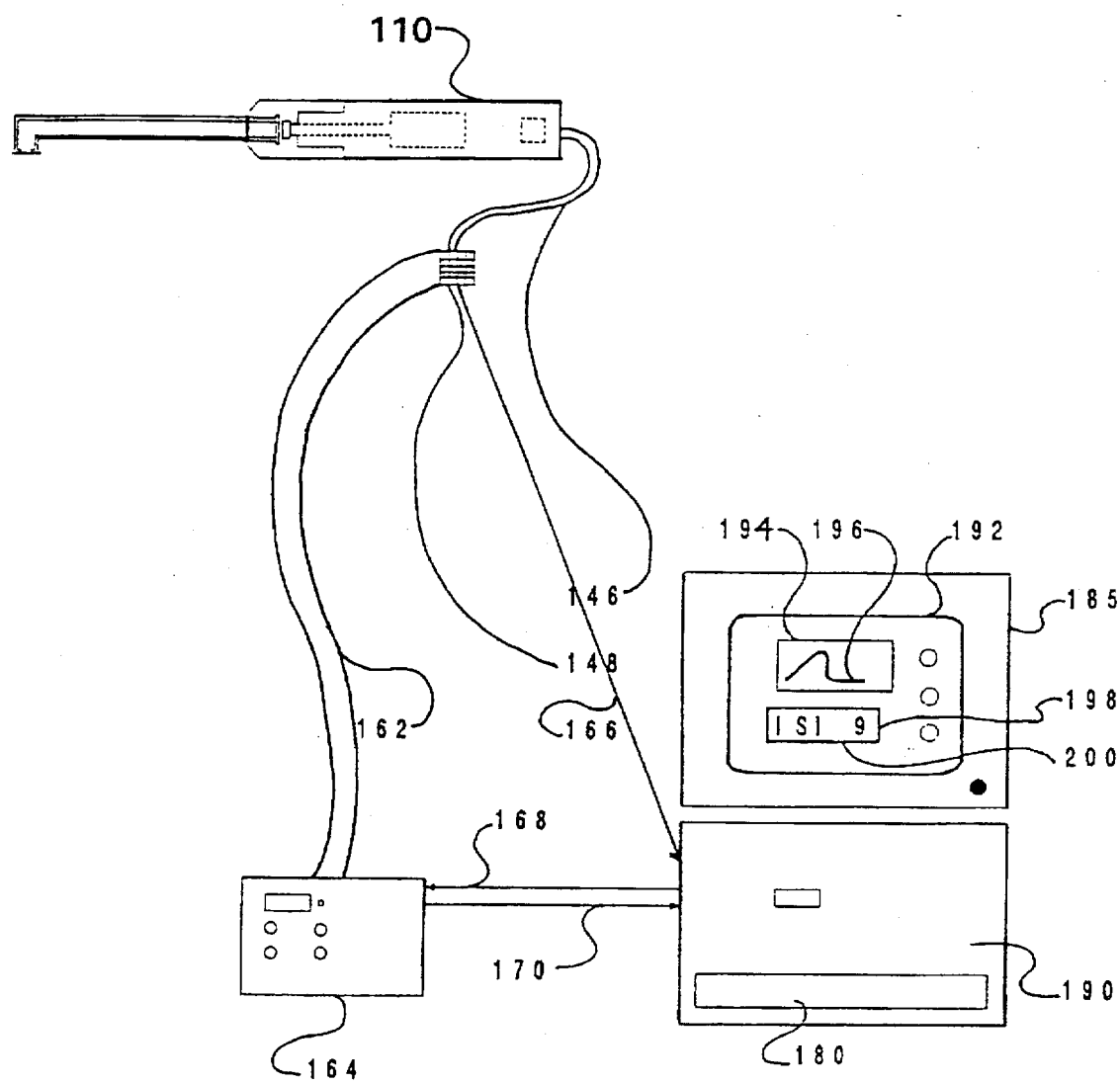
FIG. 7 is a diagram of the ACE in combination with its exterior control components showing the direction and flow of data collection and motor control signals and the resultant Index of Structural Integrity (ISI) display.

As shown in FIG. 7, the articular cartilage evaluator 110 is connected via data cable 146 to fast connector 148, which is connected via connector cable 162 to motor controller preferably an Encoder Mike Control Station 18007 of Oriel Co., Stratford, Conn., which is in turn connected to computer 190 via displacement data line 170 (containing three wires) and motion control line 168 (containing three wires). Fast connector 148 is connected to computer 190 via force transducer data line Computer 190 is preferably a Macintosh IIci with internal analog-to-digital and digital-to-analog and counter board 180, monitor 185, and screen 192. The output display consists of graph window 194 which displays a data graph 196 of displacement at a constant force over time or of force at a constant displacement over time, and index of structural integrity (ISI) window 198 in which appears the ISI display 200 preferably calculated from the data taken from measuring force data over time at a preset displacement of the articular cartilage.

In operation of the ACE 110, in a preferred embodiment, the head 130 of the ACE is inserted as shown in FIG. 5, into joint cavity 114 through small incision 116 in patient's knee 112. Then by translating or rotating the ACE 110, the head 130 is positioned perpendicularly to the articular surface of the cartilage 118 to be tested. This is easily accomplished by using the wide distal end equipped with perpendicularity rim 120 which is in contact with articular cartilage 118 and allows a large contact area between the distal end of head 130 and the articular cartilage. The entire test takes only a few seconds. Thus, there is no need to immobilize the instrument with an external positioning system. The perpendicularity rim 120 is pressed firmly against the surface of the articular cartilage by the operator and prevents movement of the ACE as a result of the resistance of the articular cartilage against the testing tip. If external mechanical support is needed, a kinematic assembly which includes a flexible arm consisting of serial spherical joints and a slide system for vertical positioning can be used to immobilize the ACE with respect to the joint.

A computer-based closed-loop speed control system as shown in FIG. 7 controls the process of data acquisition and display. The motor controller 164 of FIG. 7 commands the motor 144 in the handle of the ACE, seen in FIG. 6. For example, with reference to FIG. 6, the motor 144 moves the motor shaft distally forward, at a constant speed of 189 µm per second (which corresponds to 100 µm per second movement of the testing tip 122), and computer-based data acquisition begins. This movement is translated to testing tip 122 which is preferably a 0.5 mm or less diameter, flat-ended, rigid, porous tip, by the following route: first the horizontal motion of the motor 144 is passed through motor shaft 140 by means of contact between the head of the motor shaft 143 and steel bearing 136 to linearly moving shaft 131. Contact retaining spring 138 is pre-loaded between fixed spring retainer 152 and movable spring retainer 134. This allows motor shaft 140 to always be in contact with steel bearing 136. The tapered ends of motor coupler 142 engaging the distal side of fixed spring retainer 152 cause compression of contact retaining spring 138 when linearly moving shaft 131 moves in the distal direction.

The motion of linearly moving shaft 132 is translated via slider 131 which is preferably attached to the distal end of shaft 132 using two screws (see FIG. 8) to slide 133 by a preset ratio, preferably 1.89:1 (i.e., when the linearly moving shaft 132 moves 1.89 µm axially to the motor shaft, slide 133 moves 1 µm normal to the test surface.) As will be appreciated by those skilled in the art, this ratio can be varied by varying the slope of the top of loading wedge 126. The slide 133 is preferably attached to loading wedge 126 using two screws (see FIG. 11). Downward movement of the slide thus causes corresponding downward movement of loading wedge 126. Details of the distal or head end of the ACE are shown in FIGS. 8, 15, 16 and 17. Since the force transducer 124 abuts loading wedge 126, the former also displaces vertically by the same amount, causing force transducer probe 125 to push against testing tip 122, which moves vertically downward against and into the articular cartilage.

Figure 16:
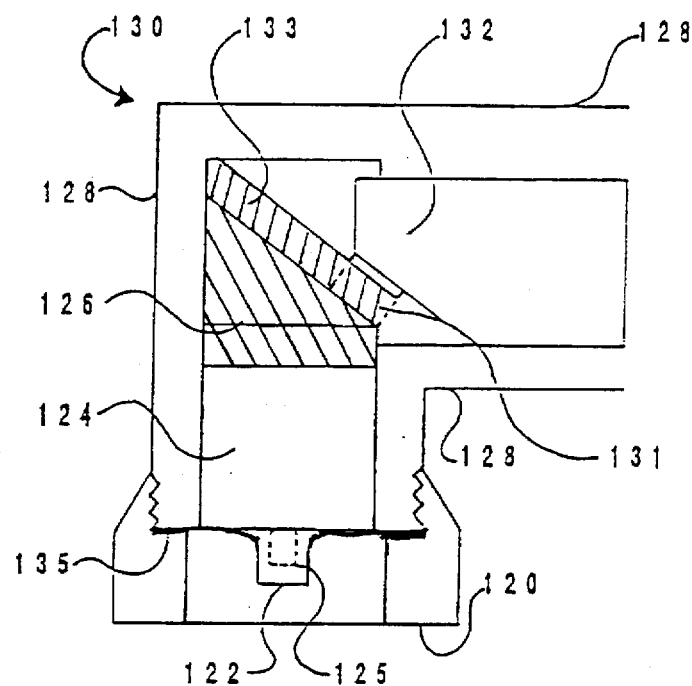
FIG. 16 is an enlarged side view of the head with the testing tip in the inactivated or fully retracted position.
Figure 17:
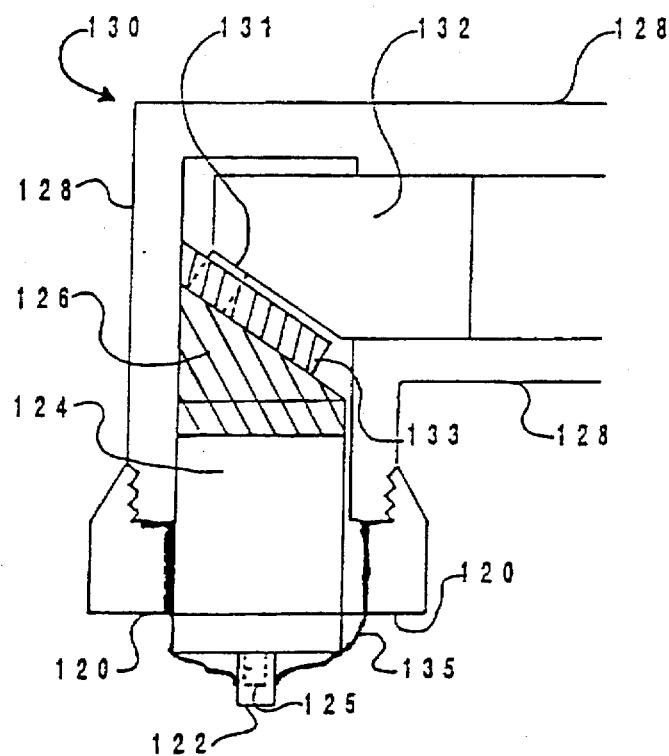
FIG. 17 is an enlarged side view of the head with the testing tip in the activated or fully extended position.

FIG. 16 shows the head 130 of the ACE with testing tip 122 in the "up" or inactivated position, and FIG. 17 shows the head 130 of the ACE with testing tip 122 in the "down" or activated position. (FIG. 17 shows a maximum activated position for the ACE. In practice when perpendicularity rim 120 rests against articular cartilage, the bottom surface of force transducer 124 will not extend beyond perpendicularity rim 120 unless the cartilage surface is substantially concave). Movement in the distal direction by linearly moving shaft 132 causes slider 131 which is fixedly attached to the underside of linearly moving shaft 131 and engaged with slide 133, to slide from the position shown in FIG. 17 along the length of slide 133 to the position shown in FIG. 18. Loading wedge 126 is pushed downward by the movement of slider 131, translating its motion to force transducer 14 and to force transducer probe 125 which pushes against testing tip 122, causing it to move through perpendicularity rim 120 and to push into and indent the articular cartilage.

As loading wedge 126 pushes against force transducer 124, the latter is activated to produce an electrical signal proportionate to the force applied against the articular cartilage 118 by testing tip 122. The output and input signals of the force transducer 124 are brought via force transducer excitation and signal wires 154 (best seen in FIG. 14) along the underside of sheath 128 (best seen in FIG. 15) enclosed in transducer excitation and signal wire tube 150 into the space inside motor coupler 142 (best seen in FIG. 6) and preferably through the casing 145 for motor 144 to data cable 146 and thence to fast connector 148. Input signals to the motor 144 are also sent via data cable 146 to fast connector 148. Output signals from the position detector 156 are transferred via position detector data wires (not shown) to data cable 146, and thence to fast connector 148.

When initiating testing, the operator sets the computer to indicate which portion of the body is being tested. As seen in FIG. 7, the force data read from the force transducer 124 are transmitted via force transducer data line 166 from the fast connector 148 to the computer 190. The data for data graph 196 start automatically being collected when the force becomes larger than a predetermined amount, preferably $9.8 \times 10^{-3}$ N. The articular cartilage deformation is monitored with the position detector (encoder) 156 (seen in FIG. 6), preferably having a 0.1 µm resolution. Its output is collected and sent to computer board 180 via position detector data wires carried by data cable 146, fast connector 148, connector cables 162, motor controller 164, and displacement data line 170. The motor keeps moving at the above speed until the articular cartilage displacement reaches a preset value, preferably 10 µm. Data points are collected and plotted on data graph 196 displayed on graph window 194 of screen 192 of monitor 185.

Using the data collected and displayed as data graph 196, a computer algorithm is used to obtain the Index of Structural Integrity (ISI) resulting in ISI display 200. The ISI is a number from one to ten which can be used by the orthopaedist to evaluate the state of health or disease of the articular cartilage. The programs for controlling the ACE, generating the data graph 196 and the ISI display 200 are preferably written in LabView object oriented language (National Instruments, 6504 Bridge Point Parkway, Austin, Tex. 78730), and run on a Macintosh II ci (8 MB RAM).

Figure 18:
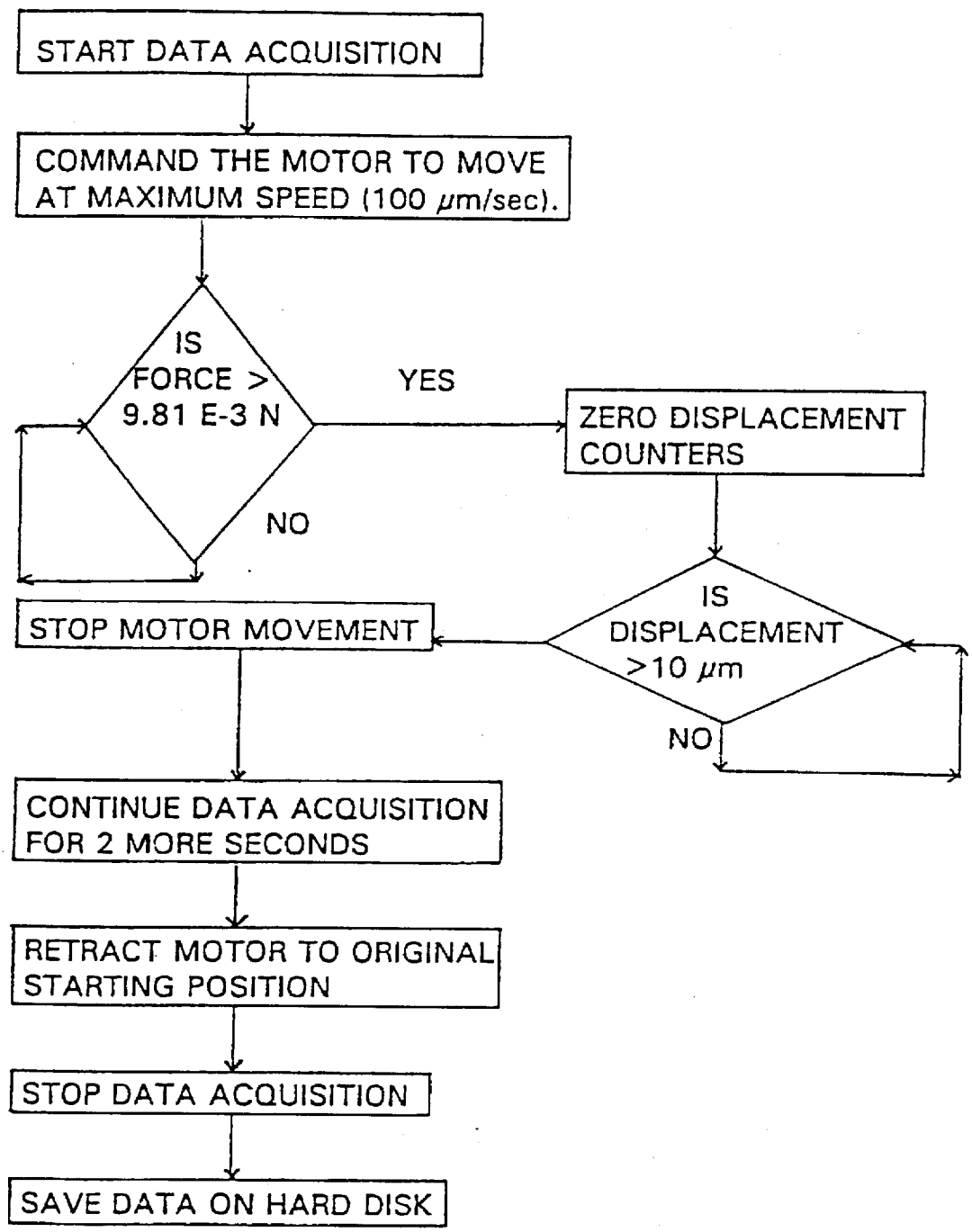
FIG. 18 is a flow diagram of steps used to perform the measurements and control the ACE of this invention as required to calculate the ISI.
Figure 19:
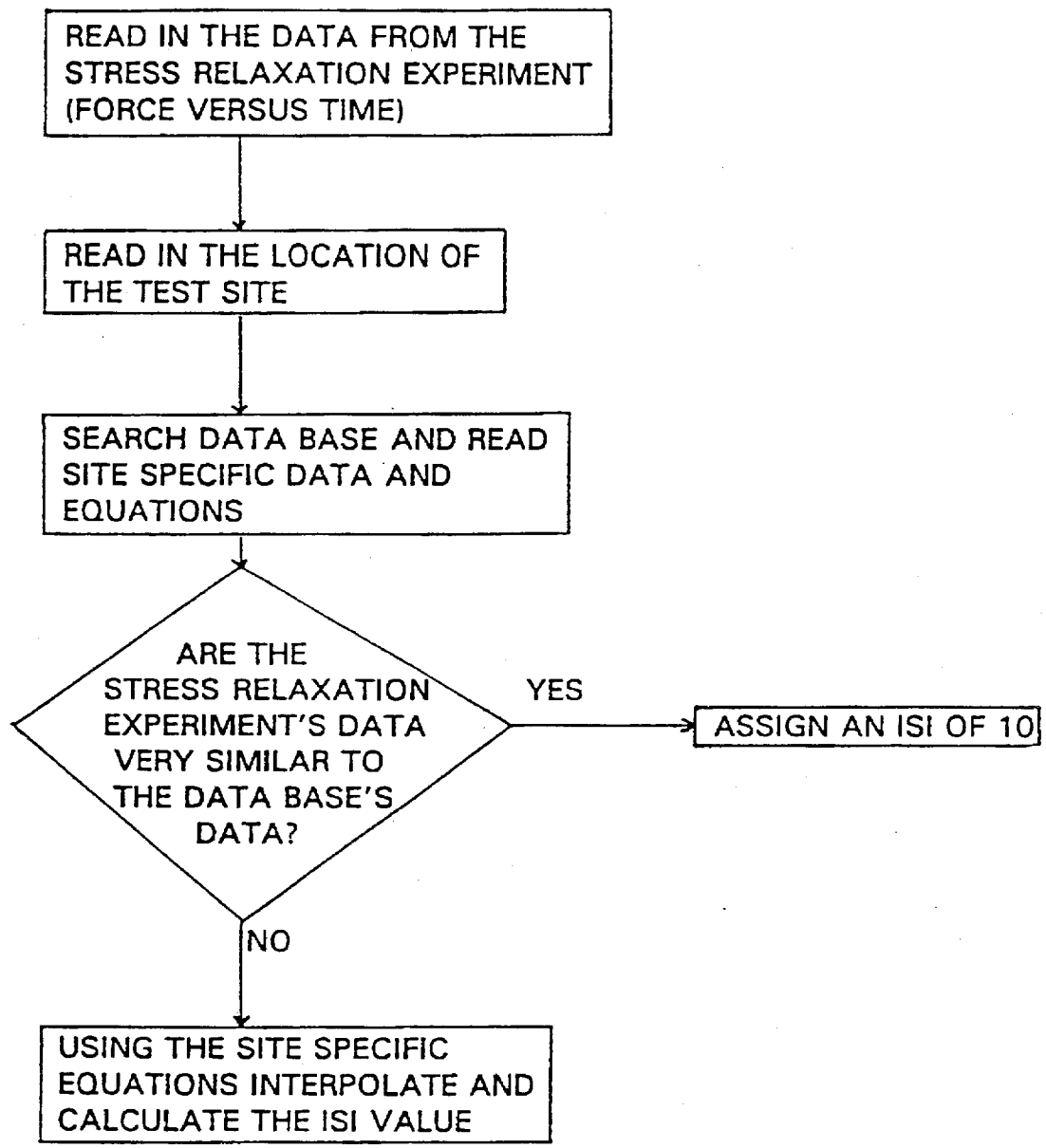
FIG. 19 is a flow diagram of steps used to measure and display the Index of Structural Integrity (ISI).

The algorithm used to control the ACE during data acquisition is shown in FIG. 18. The algorithm used to generate the ISI display using stress relaxation is shown in FIG. 19. The ISI is calculated after taking into consideration site specific data from a data base. Site specific data means data taken from tissue of the same type, i.e. from the same location in the body as that being tested. The method for generating the ISI comprises the steps of:

(a) indenting the cartilage to a predetermined displacement using a testing tip, and measuring the force required to achieve said displacement, preferably over time;

(b) determining, preferably using a computer, the ratio of said force or force versus time measurement to at least one corresponding measurement of tissue of the same type and of a known state of health, preferably healthy tissue. The measurement for the tissue having a known state of health may be a mean of a number of different measurements, preferably at least about twelve. The measurement for the healthy tissue is preferably assigned a numerical value of ten (the ISI).

(c) displaying said ratio as an integer from one to ten.

The measurements used to calculate the ISI may be stress relaxation data or creep deformation data, peak force required to achieve a predetermined indentation, area under the curve of a stress relaxation graph (preferably over a one second period), or most preferably peak force required to achieve a predetermined indentation multiplied by the amount of time required to reach this peak.

In a preferred embodiment, a database accumulated of the same data for healthy tissue taken from various locations in the body allows the measurements of the tissue being tested to be compared with healthy tissue of the same type. The operator sets the computer for the location in the body of the tissue being tested so that the test data will be compared with measurements for normal tissue of the same type.

At the end of a preset period, preferably one second, the computer 190 sends a binary signal to the motor controller (indexer) 164 which commands the motor to move at a constant speed, preferably 189 μm/sec (which corresponds to 100 μm per second movement of the testing tip 122), but this time in the opposite direction (away from the tissue). Linearly moving shaft 132 then moves toward motor 144, causing slider 131, sliding in the proximal direction on slide 133 to pull loading wedge 126, force transducer 124 and force transducer probe 125 upward whereby contact is maintained between bearing 136 attached to linearly moving shaft 132 and motor shaft 140. Testing tip 122 then retracts because it is attached to force transducer probe 125.

The ACE can then be removed from the joint cavity 114 and appropriate therapeutic measures taken based on the ISI reading displayed.

The entire mechanical test takes about one second. Preferably, the data collected are stress relaxation data, i.e. measurement of force exerted by the articular cartilage over time preferably under a step displacement, although as will be appreciated by those skilled in the art, the device may be as readily used to generate the ISI display using creep deformation data, i.e. measurement of articular cartilage displacement over time preferably under a step force.

The algorithm may be readily modified by using the creep deformation data instead of the stress relaxation data to generate the ISI display using creep deformation data.

In a preferred embodiment, the ACE is sensitive enough to apply and measure forces and displacements such that the thickness of the articular cartilage exerts a negligible effect (preferably less than about 0.10 percent, and more preferably less than 0.05 percent) on the reaction of the articular cartilage to indentation. For example, as is known in the art, the reaction of articular cartilage to a substantially small strain is unaffected by the tissue's thickness. When indentations on the order of 10 μm are used, the thickness of the articular cartilage need not be measured because the total strain applied as a result of such a small deformation is minuscule (about 0.04 percent). As such, calculating the material properties of the tissue, such as apparent compressibility (Poisson's ratio) compressive stiffness (aggregate modulus) and permeability is not needed for generation of the ISI. In addition, in such case thickness measurement is not required for determining the ISI. However, material properties may also be calculated using the device of this invention. Thickness measurements are not required for such calculations and they can be approximated as long as the applied strain or stress is substantially small.

For the above reasons, in a preferred embodiment, the cartilage evaluator includes a loading system which is adapted to indent less than about 20, 30, or 50 microns during use, and preferably less than about 10 microns during use. In general, less cartilage indentation results in less damage or harm (whether real or potential) to the cartilage.

In a preferred embodiment the cartilage evaluator is adapted to measure the response of cartilage in less than about 10, 20, or 30 seconds, and more preferably less than about 1 second to about 5 seconds, during use. In such circumstances, the practitioner can quickly move the evaluator over different portions of the cartilage, rapidly stopping to obtain "spot" evaluations of the response and material properties of the cartilage during use.

Significantly, the cartilage evaluator of preferred embodiments of this invention may be adapted to evaluate the cartilage during use without harming to any portion of the cartilage. As such, the nondestructive nature of this evaluator enables the practitioner to use the evaluator to widely, carefully, and unsparingly scan different portions of cartilage without fear of doing more harm by testing than would have resulted if no testing was conducted.

As shown in FIG. 15, in a preferred mode the inside diameter of the perpendicularity rim 120 is at least 5–10 times the diameter of testing tip 122. In this manner, strain and other surface factors created when the cartilage contacts the edges of perpendicularity rim 120 are inhibited from propagating and/or affecting cartilage that contacts the testing tip 122.

Figure 20:
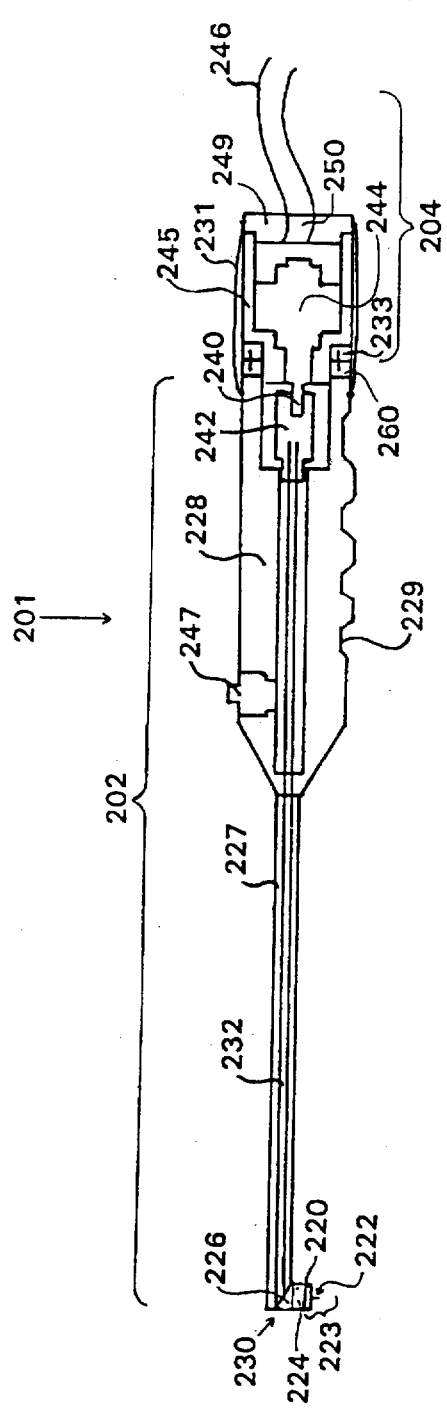
FIG. 20 depicts the Actaeon™ embodiment of the invention having a disposable distal end and a reusable proximal end containing the motor assembly.

Another embodiment of the hand-held articular cartilage evaluator, referred to as the Actaeon™ probe, comprises a disposable section including the head, and a detachable reusable portion comprising the motor. This embodiment is shown in FIG. 20. The Actaeon™ probe 201 comprises a disposable probe assembly 202 comprising a head 230 which comprises testing tip 222, perpendicularity rim 220, force transducer 224, loading wedge 226 and other components of the head similar to those described above in connection with the ACE embodiment. The Actaeon™ also comprises a linearly moving shaft 232, a shaft sheath 227, and a handle sheath 228. The perpendicularity rim 220, testing tip 222 and membrane (not shown) holding the testing tip 222 to perpendicularity rim 220 may be detachable as a replaceable tip assembly 223, or may be non-detachable. The disposable assembly also comprises a thumb trigger switch 247. The linearly moving shaft 232 is connected to motor 244 by means of motor coupler 242. To the proximal end of handle sheath 228 is attached connector 260. The Actaeon™ embodiment also comprises a reusable motor assembly 204 at the proximal end thereof, comprising a motor 244 surrounded by motor case 245 at the distal end and around the circumference thereof, and by motor case end 249 and wire holder 250 at the proximal end of reusable motor assembly 204. Flexible wire data cable 246 extends out from wireholder 250 at the proximal end of the reusable motor assembly 204. Prophylactic seal 231 extends from the proximal end of handle sheath 228 to fasten to the outer rim of motor case end 249. The ends of prophylactic seal 231 may be rolled or thickened to fit into grooves (not shown) on motor end 249 and handle sheath 228 so that the seal remains in place when stretched. Alternatively, an O-ring may be used.

Motor case 245 is equipped with proximal electrical contacts 233 abutting connector 260 at the proximal end of handle sheath 228. The bottom of the enlarged portion of handle sheath 228 is formed into ridges and grooves to serve as a pistol-type handgrip 229.

Figure 21:
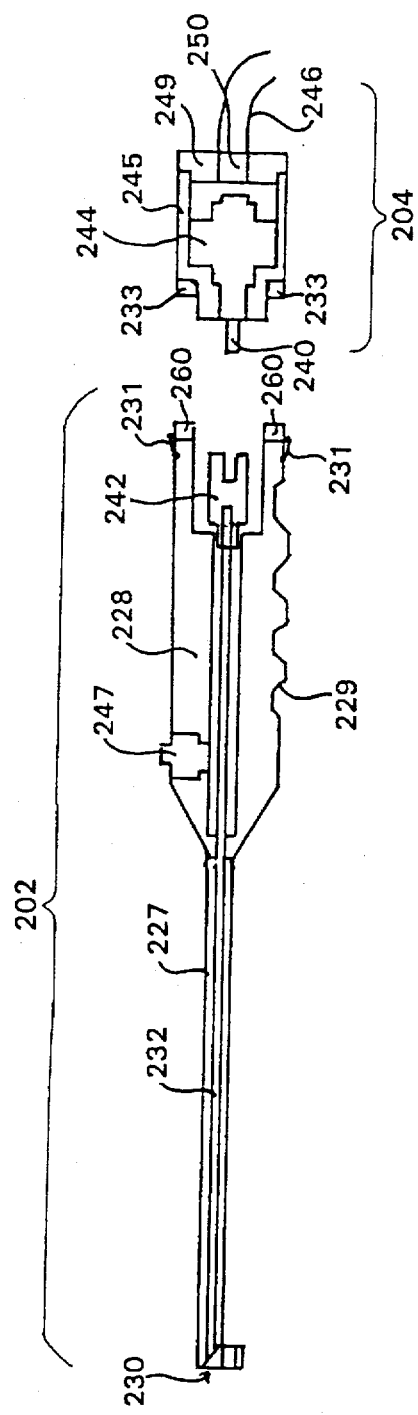
FIG. 21 depicts the separated disposable and reusable sections of the Actaeon™.

As shown in FIG. 21, the device is separable into a disposable part comprising the disposable probe assembly 202 including the head 230, linearly moving shaft 232, shaft sheath 227, handle sheath 228, thumb trigger switch 247, hand grip 229, motor coupler 242, connector 260 and prophylactic seal 231; and a reusable motor assembly 204 comprising the motor 244, motor shaft 240, motor case 245, proximal wire contacts 233, and motor case end 249 with wire holder 250 connected to flexible wire data cable 246 containing wires as described above in connection with the ACE.

Figure 22:
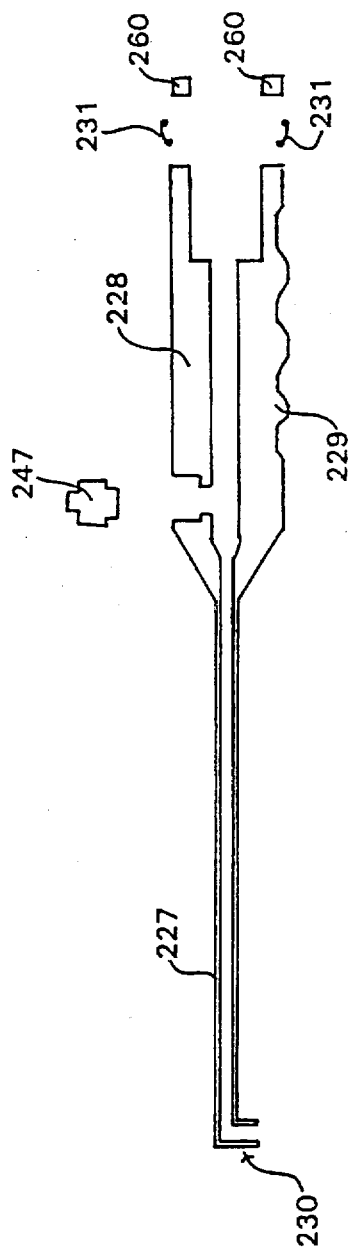
FIG. 22 depicts the sheaths for the shaft and handle, the thumb trigger switch, distal electrical contacts and prophylactic seal of the Actaeon™.
Figure 23:
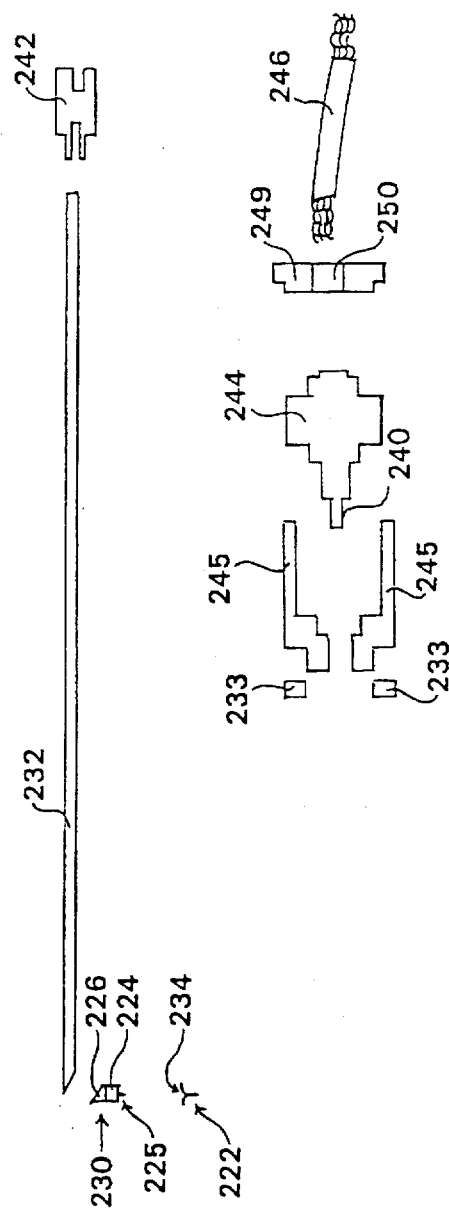
FIG. 23 is an exploded view of the Actaeon™.

FIGS. 22 and 23 are exploded views of the device. FIG. 22 shows the shaft sheath 227 and handle sheath 228, with hand grip 229, thumb trigger switch 247, prophylactic seal 231, and connector 260. The shaft sheath 227 and handle sheath 228 are preferably injection molded as one piece of a plastic such as medical grade polycarbonate.

FIG. 23 shows the linearly moving shaft 232, the loading wedge 226, force transducer 224, force transducer probe 225, detachable membrane 234 and testing tip 222, proximal electrical contacts 233, motor case 245, motor 244, motor case end 249 and wire holder 250, flexible wire data cable 246 and motor coupler 242. The head also comprises a slide and slider similar to that shown in FIG. 8, such as a square ways or rectangular ways slider.

Figure 24:
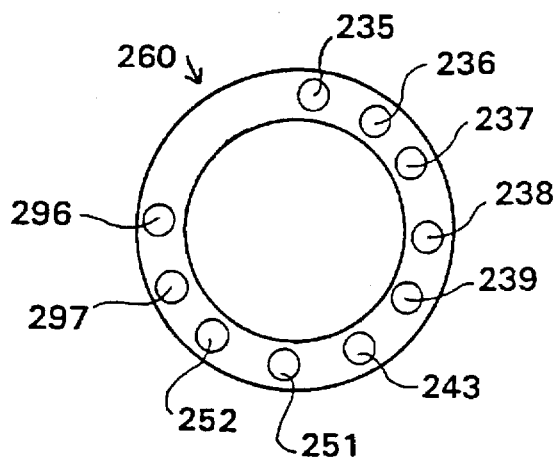
FIG. 24 illustrates the electrical connector and system used to identify the various head angles available.

FIG. 24 shows connector 260 made of nonconductive material which lies between the disposable and reusable probe assemblies 202 and 204 of the device and forms part of the disposable probe assembly 202. The connector 260 is equipped with conductive common angle bit 235, conductive bits one 236, two 237 and three 238 which provide an indication of the angle of orientation of the head (see FIG. 27) and force transducer contact (positive excitation) 239, force transducer contact (negative excitation) 243, force transducer contact (positive signal) 251 and force transducer contact (negative signal) 252, as well as first switch wire contact 296 and second switch wire contact 297.

Figure 25:
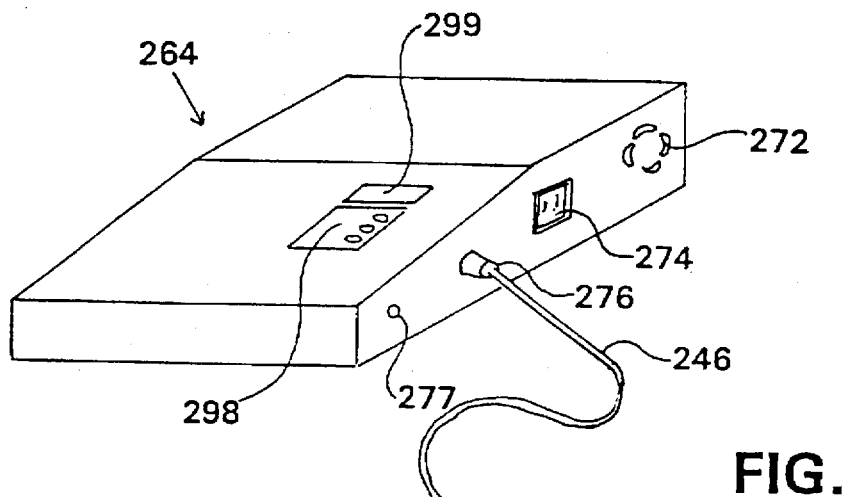
FIG. 25 depicts the portable controller connected to the Actaeon™ via a cable.

FIG. 25 depicts a perspective view of the Actaeon™ probe 201, showing shaft sheath 227, handle sheath 228 and head 230, connected by flexible wire data cable 246 via data cable plug 276 to controller 264, a computer comprising AC line receptacle 274, fan 272, and serial port 277 which may be used for connecting the controller to another computer 190 (FIG. 7). The controller 264 preferably is not, however, connected to another computer but rather contains a custom-made circuit board (not shown) comprising an EEPROM with the program needed to run the probe. Controller 264 has a keypad 298 for running and calibrating the Actaeon™ (and may include other control functions) and a liquid crystal display 299. The controller 264 also preferably has a rechargeable battery (not shown) and an intelligent charger (not shown) so that the system comprising the Actaeon™ probe 201 and controller 264 is completely portable.

Figure 26:
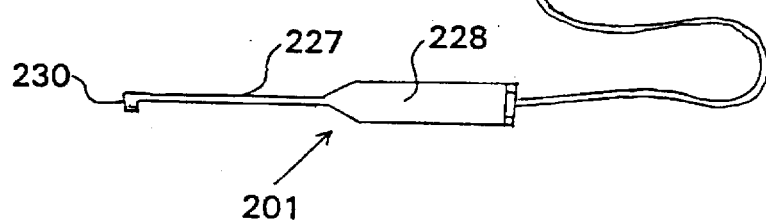
Figure 26:
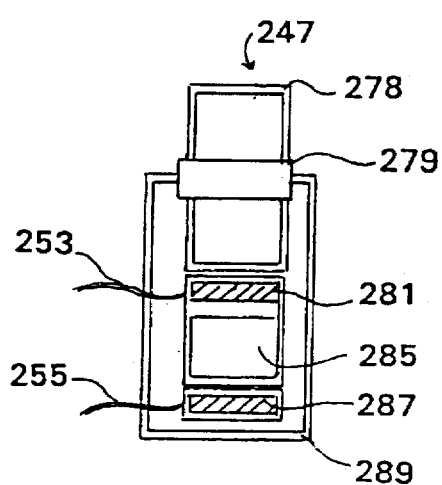

FIG. 26 provides details of thumb trigger switch 247. The thumb trigger switch 247 comprises a plunger 278 extending into the body of switch 247 through plastic casing 289 via O-ring 279. Beneath plunger 278 and spaced apart therefrom lies an upper copper disk 281 immediately above and in contact with a layer of conductive plastic foam 285. Beneath the conductive plastic foam 285 and spaced apart therefrom lies lower copper disk 287. Upper copper disk 281 is attached to first switch wire lead 253 and lower copper disk 287 is attached to second switch wire lead 255.

FIG. 27 depicts several embodiments of the Actaeon™ probe having different head angle orientations. FIG. 27A shows head 230 at an angle of 30° from shaft sheath 227; FIG. 27B shows head 230 at an angle of 45° from shaft sheath 227; FIG. 27C shows head 230 at an angle of 60° from shaft sheath 227; FIG. 27D shows head 230 at an angle of 90° from shaft sheath 227; FIG. 27E shows head 230 at an angle of 120° from shaft sheath 227.

The reusable motor assembly 204 of the Actaeon™ probe 201 preferably has a length of less than about 10 cm, more preferably about 7 cm, with the handle sheath 228 being about 10 cm in length and the shaft sheath 227 including the head 230 being about 15.3 cm in length. The controller 264 is preferably about 25.4 cm in width, about 28.0 cm in length, and about 7.6 cm in height.

In use, the reusable assembly 204 of the Actaeon™ probe 201 is connected to the disposable handle assembly 202 by means of double female motor coupler 242 which links the two parts, preferably by snapping onto the male proximal end of linearly moving shaft 232. Linearly moving shaft 232 may be equipped with an annular ridge (not shown) which snaps into place into an annular groove (not shown) in motor coupler 242 or a spring-loaded ball snap. Motor coupler 242 is connected to motor 244 by a similar arrangement whereby the male distal end of motor shaft 240 is inserted into the female proximal end of motor coupler 242. The motor 244 and motor coupler 242 are encased and held together by motor case 245, having a distal opening through which motor shaft 240 projects such that it may be inserted into motor coupler 242.

An incision large enough to accommodate head 230 of the probe is made in skin and tissue overlying a patient's cartilage as shown in FIG. 5, and perpendicularity rim 220 is placed against the cartilage, touching the cartilage at all points around its circumference. This ensures perpendicular placement of the testing tip 222.

The testing tip 222 of the Actaeon™ probe 201 is attached to membrane 234 (FIG. 23), which is in turn attached to perpendicularity rim 220, in such a way that the testing tip 222 is moved downward into the cartilage when displacement force is exerted against it. The probe is pre-calibrated during manufacture.

Displacement force exerted laterally by motor 244 in the distal direction is communicated to linearly moving shaft 232, and thence to loading wedge 226, and successively to testing tip 222, and cartilage.

The Actaeon™ 201 is readied for use by pressing the activation button on keypad 298. The motor 244 is then actuated to exert displacement force against the cartilage by depression of thumb trigger switch 247, best seen in FIG. 26. Activation of plunger 278 by means of thumb pressure pushes upper copper disk 281 and conductive plastic foam 285 downward so that the latter is in contact with lower copper disk 287, closing the circuit between first switch wire lead 253 and second switch wire lead 255. These wire leads are connected respectively to first and second switch wire contacts 297 and 296 (seen in FIG. 24), and thence current flows through these contacts to controller 264 (FIG. 25). Capacitance or resistance of the conductive foam 285 changes with pressure and when it reaches a predetermined value, current is allowed to flow to activate the probe. The conductive foam 285 may act like a force transducer, changing in resistance as it is deformed by the pressure applied upon it by upper copper disk 281. When a predetermined resistance value has been reached, the computer in controller 264 activates the motor 244.

The operator is encouraged to push the thumb trigger switch 247 slowly, moving up to about 500 g to about 1000 g of pressure. Pushing the plunger 278 tends to create a moment of force around the plunger making the head 230 rotate down. When the plunger is pushed down slowly the measurement (which is completed in about a half second) can be completed before an appreciable moment of force develops.

The controller is capable of controlling the amount of displacement produced by the motor, the speed and the duration of displacement.

Upon receipt of the signal resulting from activation of thumb trigger switch 247, the computer in controller 264 sends a signal via flexible wire data cable 246 through wire holder 250 in motor case end 249, to motor 244. Motor 244 is activated to move motor shaft 240 forward, i.e., in a distal direction, in one micron increments. The controller 264 is calibrated such that one pulse received from the controller 264 is translated into approximately one micron displacement. This horizontal displacement is transmitted via linearly moving shaft 232 to loading wedge 226 where it is translated to vertical displacement of the testing tip 222. The force transducer 224 is excited via positive and negative force transducer contacts 239 and 243 (not shown) and signals the force exerted on it back to the controller 264 via leads (not shown) from force transducer 224 via positive and negative force transducer signal contacts 251 and 252. When the controller 264 registers a sudden increase in force signalled by force transducer 224, it commands motor 244 to move motor shaft 240 forward rapidly, to displace the testing tip about 50 μm. When the testing tip displacement reaches 50 μm, the controller 264 registers the peak force signalled by the force transducer 224, and may calculate the ISI or other parameters as described above. The ISI or other data from the force versus time profile is then displayed on the liquid crystal display 299 of controller 264.

After registering the peak force data, the controller 264 commands the motor 244 to reverse quickly and smoothly, displacing the motor shaft 240 in a proximal direction a distance equal to the total distal displacement previously exerted, such that the testing tip 222 is withdrawn from the cartilage and returned to its initial position.

As shown in FIG. 27, the head may be angled relative to the shaft. The angle of the head will affect the ratio of horizontal to vertical displacement exerted by the probe. Disposable probe assemblies 202 are configured such that an electrical connection is made between the disposable probe assembly 202 and the controller 264 via common angle bit 235 which is used for disposable probe assemblies of all angles, and one of bits one 236, two 237, or three 238. Since there are three bits dedicated to signalling the head angle to the computer, and only one will have current flowing through it, there are eight different possible configurations of current flow which can be recognized by the computer and eight different head angles can therefore be recognized. The connection with a particular bit signals the controller 264 that a particular head angle is being used so that the displacement exerted by motor 244 can be adjusted in accordance with the ratio between horizontal displacement exerted by the linearly moving shaft 232 and the testing tip 222. Calculations for such adjustments are known to the art.

Perpendicularity rim 120 or 220 may be equipped on its distal surface with pieces of pressure-sensitive piezo electric film (not shown) which act as pressure-sensitive force transducers placed at several points around its circumference. The pieces of film are connected to controller 264 and/or computer 190 whereby a signal is generated when all of the pieces are touching cartilage so as to assure perpendicularity. The computer may also be programmed not to make a measurement if the testing tip has been moved more than a given distance beyond the perpendicularity rim 120 or 220 before encountering cartilage. For example, if the tip moves more than 145 μm before encountering cartilage, this would indicate a 2° or greater deviation of the testing tip from perpendicular. Pressure-sensitive piezo electric film may also be substituted for the force transducer 124 or 224 and the device can be accordingly miniaturized.

In an improved embodiment of this invention shown in FIGS. 5-17, the screw-on replaceable tip assembly 123 (FIG. 15) comprising perpendicularity rim 120, testing tip 122 and membrane 135, may be replaced by a snap-on replaceable tip assembly.

Figure 28:
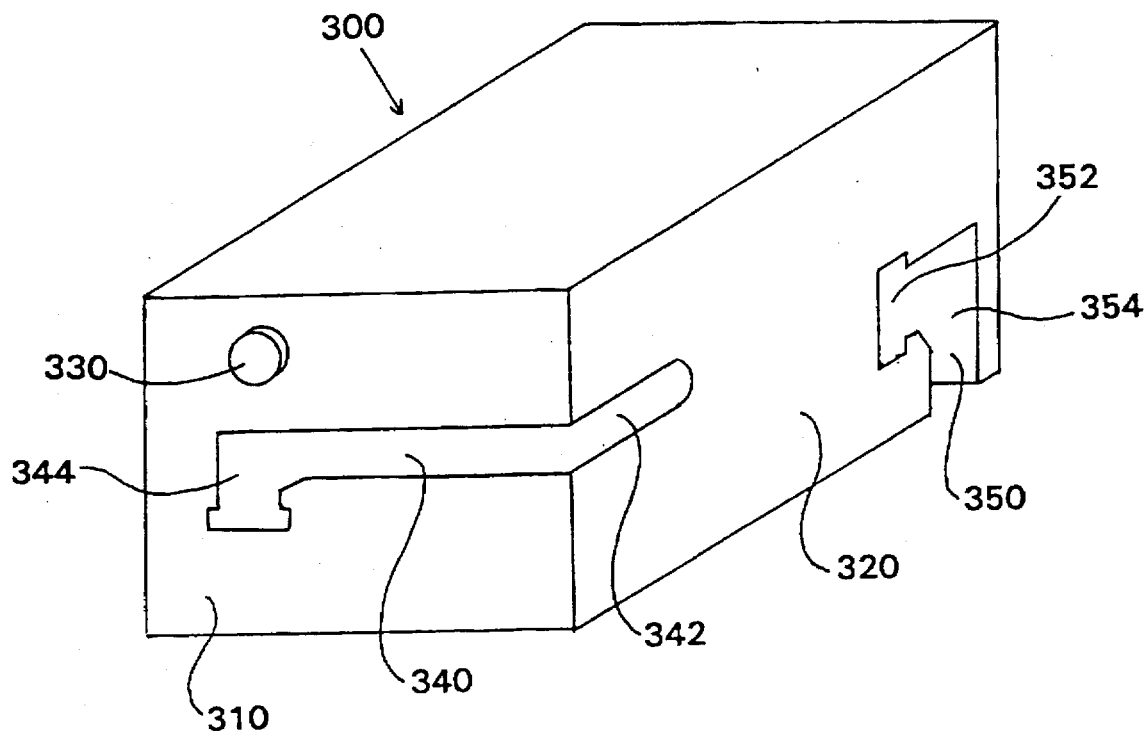
FIG. 28 is a perspective view of the calibrator for the ACE.

The probes of this invention may be calibrated before sale to the ultimate user, or may be calibrated in a device especially designed for that purpose such as the calibrator 300 shown in perspective in FIG. 28. The front surface 310 is equipped with a release button 330 and a calibration slot 340 which extends into side 320 of the calibrator. Calibration slot 340 is shaped so as to accommodate the distal end of the articular cartilage evaluator (ACE) 110 seen disposed in said calibration slot in FIG. 30. Calibration slot 340 comprises a shaft guide 342 and a head guide 344. The calibrator 300 also comprises a tip assembly removal slot 350 disposed in side surface 320 comprising a head channel 354 accommodating the head 230 and distal portion of the shaft, and a rim channel 352.

Figure 29:
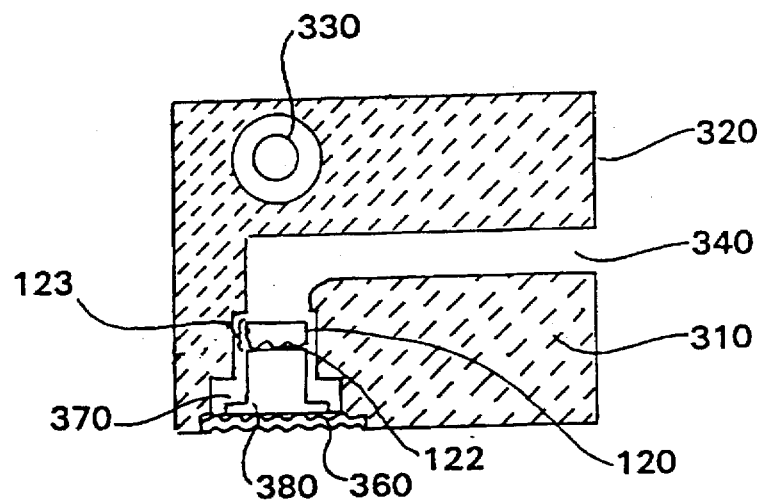
FIG. 29 is a frontal cross-section of the calibrator showing the replaceable tip assembly therein.

FIG. 29 is a frontal cross-section of calibrator 300. On the bottom floor of the calibrator 300, an elastomeric membrane 360 is disposed over a hole cut into the floor of the calibrator 300 so that the operator can push against the elastomeric membrane 360. Resting atop the elastomeric membrane 360 is testing tip platform 380 disposed within alignment cavity 370. Atop the testing tip platform 380 is replaceable tip assembly 123, which comprises testing tip 122 and perpendicularity rim 120, and which rests just below the bottom of calibration slot 340. When the operator pushes membrane 360, the testing tip platform 380 pushes replaceable tip assembly 123 upward to snap into place on the head 130 of the ACE 110.

Figure 30:
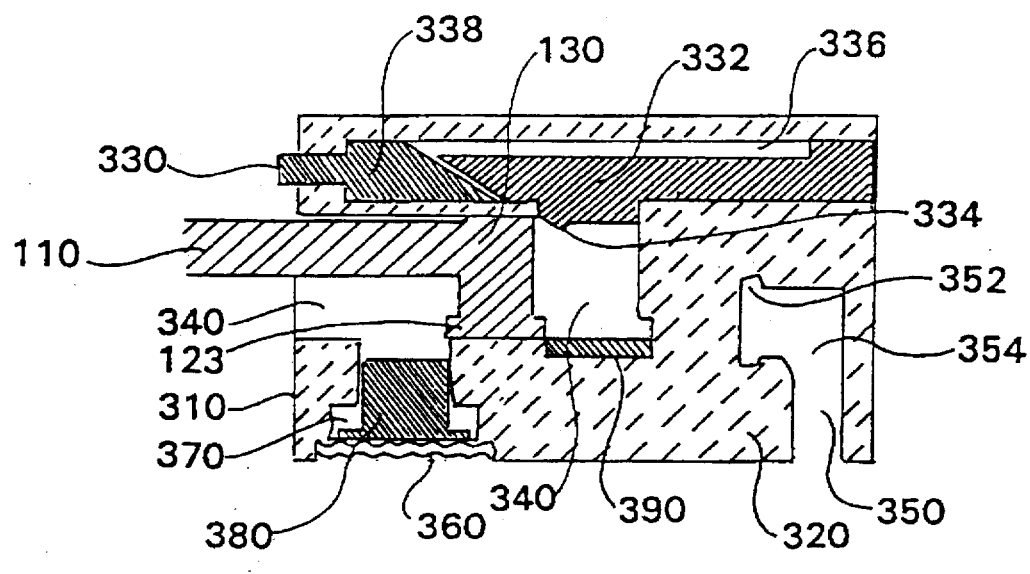
FIG. 30 is a cross-section taken from the side of the calibrator showing the mechanism for attaching the replaceable tip assembly, the mechanism for calibrating the ACE including the cantilever beam for exerting downward force on the head during calibration and releasing the head from the calibrator, as well as the slot for removal of used tip assemblies.

As seen in FIG. 30, calibration slot 340 extends further into the body of the calibrator 300 to the rear of alignment cavity 370. On the rear floor of calibration slot 340, just below the level of testing tip assembly 123, a calibration pad 390 is disposed. Release button 330 is the front end of release wedge 338 which abuts cantilever beam 332. Release wedge 338 and cantilever beam 332 extend horizontally within beam cavity 336. Cantilever beam 332 is equipped with locking tab 334 disposed above the front portion of calibration pad 390.

Figure 31:
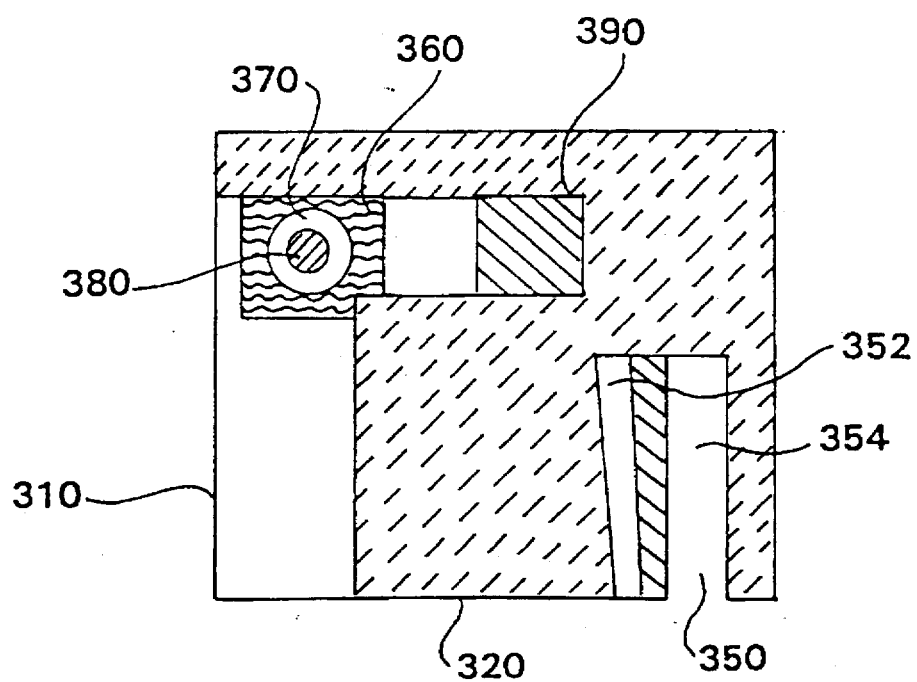
FIG. 31 is a cross-section from the top of the calibrator showing the channels for the head and rim of the ACE, whereby the replaceable tip assembly is removed.

FIG. 31 is a top cross-sectional view of calibrator 300 showing the front surface 310 and side surface 320, as well as tip assembly removal slot 350 disposed in side surface 320, comprising head channel 354 and rim channel 352 which angles away from head channel 354 toward the interior of calibrator 300.

The calibrator 300 is designed to attach a fresh replaceable tip assembly 123 to head 130 of the articular cartilage evaluator (ACE) 110. To attach fresh replaceable tip 123, the operator inserts the head 130 of pre-sterilized ACE 110 into calibration slot 340, holding the ACE 110 so that the long axis thereof lies in a direction perpendicular to the long axis of calibrator 300, and the proximal end of the ACE 110 sticks out of the shaft guide 342 of calibration slot 340 to the side 320. As shown in FIG. 28, shaft guide 342 extends only partway, i.e., about an inch, into the rear of calibrator 300. When the ACE 110 touches the rearmost wall of shaft guide 342, the head 130 of the ACE 110 is disposed above replaceable tip assembly 123 which is atop testing tip platform 380 in alignment cavity 370. The operator then presses upward from the bottom of calibrator 300 on elastomeric membrane 360, which in turn presses testing tip platform 380 upward, causing testing tip assembly 123 to snap into place on the distal end of the head 130 of the ACE The operator then rotates the ACE 110 90° so that the proximal end thereof extends out the front surface 310 of the calibrator 300 with the long axis of the ACE 110 lying parallel to the long axis of the calibrator 300. The operator then pushes the ACE 110 toward the rear of the calibrator 300 as shown in FIG. 30 until the head 130 contacts locking tab 334.

As the operator continues to push head 130 as far as possible to the rear of calibration slot 340, locking tab 334 presses head 130 down into calibration pad 390 with a predetermined force, e.g., 5 N. Locking tab 334 and cantilever beam 332 are formed of a flexible material which provides the appropriate downward force. Calibration pad 390 has a known stiffness. The operator then activates the ACE 110 so that testing tip 122 indents calibration pad 390.

The ACE 110 measures peak force exerted against the calibration pad 390 as described hereinabove. If the measurement does not correspond to the known stiffness of the calibration pad 390, the computer 190 either provides a message that the probe is defective or applies the appropriate correction factor (which should not be less than 10 percent of the original number) to the calibration equations such that a correct value for peak force exerted against testing tip 122 would result. If the correction factor is more than 10 percent of the original number, the liquid crystal display 299 displays a message that the probe is defective. If the correction factor is less than 10 percent of the original number, the operator then recalibrates the ACE 110 against the calibration pad 390 to ensure it has been correctly calibrated. The ACE 110 is then ready for clinical use to test cartilage in vivo using the correction factor.

After the calibration has been performed, the operator depresses release button 330, which moves release wedge 338 backward so that it slides along cantilever beam 332 which is made of flexible material such that it is forced upward, releasing the downward force being exerted against the head 130 of the ACE 110 by locking tab 334 so that the ACE 110 may be easily removed from calibrator 300.

After use, the head 130 of the ACE 110 is removed from the patient's body and inserted into tip assembly removal slot 350 of calibrator 300. As the head 130 is pushed into the interior of calibrator 300, the head and distal portion of the shaft is accommodated in head channel 354 and the replaceable tip assembly 123 is accommodated in rim channel 352. The rim channel 352 angles away from head channel 354 as shown in FIG. 31 so that when the shaft of the ACE 110 is pushed straight into the calibrator 300, the replaceable tip assembly 123 is forced away from the head 130, and removed therefrom.

The ACE 110 may then be removed from calibrator 300 and sterilized for re-use. In a preferred embodiment, the calibrator is disposable and is not re-used.

The foregoing description of the present invention has been directed to particular preferred embodiments. It will be apparent, however, to those skilled in the art that modifications and changes in the various devices and methods described above may be made without departing from the scope and spirit of the invention. For example, any computer-based, closed-loop feedback system incorporating a motor, a positional detector, with or without a force transducer, may be made without departing from the scope and spirit of the invention regardless of how the various components are arranged or coupled to each other provided the resulting measurements are acquired using an automatic computer-based system. Therefore, equivalent elements may be substituted for those illustrated and described herein. Parts may be reversed, and certain features of the invention may be utilized independently of the use of other features, all as would be apparent to one skilled in the art after having benefitted from the description of the invention. As can be appreciated from the above discussion, the invention can present a practical advance over conventional manual indenter devices which, by their nature, cannot achieve the level of accuracy obtained from the computer-based closed-loop system of the present invention. Similarly, the present invention represents an advance in the art of cartilage evaluation in that it provides and displays, in the Index of Structural Integrity, a single number from one to ten which enables the physician to quickly, objectively and repeatably measure the health of a patient's cartilage tissue in vivo in his office.

What is claimed is:

1. A cartilage evaluator adapted to measure force exerted by the cartilage against the evaluator during use; comprising:
   (a) a hand-held component comprising:
      (1) a loading system comprising a testing tip for placement proximate to, and adapted for indenting the cartilage a predetermined distance during use;
      (2) an alignment system adapted to align the testing tip substantially perpendicular to the surface of the cartilage during use;
      (3) a force detection system adapted to detect force exerted by the cartilage against the testing tip over time during use;
   (b) a computer operatively connected to said loading system and to the force detection system, the computer being adapted to control the loading system and measure said force.

2. The cartilage evaluator of claim 1 wherein said loading system comprises a motor operatively connected to a motor shaft adapted to exert an axial force during use.

3. The cartilage evaluator of claim 2 wherein said loading system further comprises a force translation system connected to said motor shaft and said testing tip for changing the direction of the motion imparted to said testing tip by said motor shaft during use.

4. The cartilage evaluator of claim 3 wherein said force translation system comprises a slider fixedly attached to said motor shaft, said slider being adapted to move at an angle to said motor shaft in response to force imparted by said motor shaft during use.

5. The cartilage evaluator of claim 4 wherein said force translation system is adapted to change the speed of the motion of the motor shaft imparted to the testing tip during use.

6. The cartilage evaluator of claim 1 comprising a force transducer between the slide and the testing tip operatively connected to said computer whereby the force exerted by the cartilage against the testing tip is measured during use.

7. The cartilage evaluator of claim 1 comprising a position detector operatively connected to said computer and said loading system whereby the position of the testing tip with respect to the cartilage is measured and controlled during use.

8. The cartilage evaluator of claim 1 wherein said alignment system comprises a perpendicularity rim operatively connected to said testing tip.

9. The cartilage evaluator of claim 8 wherein the testing tip has a diameter, and wherein the perpendicularity rim has an inside diameter which is at least about 5 times greater than the diameter of the testing tip.

10. The cartilage evaluator of claim 1 comprising a replaceable testing tip assembly comprising a perpendicularity rim and a testing tip.

11. The cartilage evaluator of claim 1 comprising a disposable probe assembly and a reusable motor assembly.

12. The cartilage evaluator of claim 1 comprising means for standardizing the amount of force communicated to the distal end of the evaluator as a result of activating the evaluator, said means comprising a thumb trigger switch activated by a predetermined thumb pressure.

13. The cartilage evaluator of claim 12 wherein said means for standardizing force also comprise a pistol-type hand grip.

14. The cartilage evaluator of claim 1 comprising a head at an angle from the shaft thereof between about 30° and about 80°.

15. The cartilage evaluator of claim 14 comprising electrical means for informing the computer of the head angle, and for compensating for said head angle in calculating force exerted by the cartilage against the testing tip.

16. The cartilage evaluator of claim 1 wherein said computer is comprised within a battery-operated controller and comprises an EEPROM programmed to operate said hand-held component.

17. The cartilage evaluator of claim 1 wherein the loading system is adapted to indent less than about 50 microns during use.

18. The cartilage evaluator of claim 1 wherein the loading system is adapted to indent less than about 10 microns during use.

19. The cartilage evaluator of claim 1 wherein the cartilage evaluator is adapted to measure the response of cartilage in less than about 10 seconds during use.

20. The cartilage evaluator of claim 1 wherein the cartilage evaluator is adapted to measure the response of cartilage in less than about 5 seconds during use.

21. The cartilage evaluator of claim 1 wherein the cartilage evaluator is adapted to evaluate the cartilage during use without harming any portion of the cartilage.

22. The cartilage evaluator of claim 1 wherein the cartilage evaluator is adapted to evaluate the cartilage without determining the thickness of the cartilage.

23. The cartilage evaluator of claim 1 wherein the cartilage evaluator is adapted to evaluate articular cartilage of a human knee.

24. A system for evaluating cartilage comprising:
   (a) a hand-held component comprising:
      (1) a loading system comprising a testing tip for placement proximate to, and adapted for indenting the cartilage a predetermined distance during use;
      (2) an alignment system adapted to align the testing tip substantially perpendicular to the surface of the cartilage during use;
      (3) a force detection system adapted to detect force exerted by the cartilage against the testing tip over time during use;
   (b) a calibrator for said cartilage evaluator comprising a calibration pad having a known stiffness, said calibration pad also comprising means for attaching a replaceable tip assembly to said evaluator.

25. The system of claim 24 wherein said calibrator also comprises means for removing said replaceable tip assembly from said evaluator.

26. A computerized device for determining the state of health or disease of cartilage tissue comprising:
   (a) a force measurement system adapted to measure force exerted by the cartilage against a testing tip that is indenting the cartilage to a predetermined displacement during use;
   (b) a computer system adapted to compare the ratio of said force measurement to at least one corresponding measurement of tissue of the same type having a known state of health;
   (c) a system for expressing said ratio.

27. The device of claim 26 comprising a system for measuring force over time, a system for calculating a number representing the peak force value multiplied by the time in seconds to reach said peak value and a system for comparing said numbers with the corresponding calculated number for tissue having a known state of health.

28. The device of claim 27 wherein said corresponding tissue measurement comprises the mean of at least about twelve measurements of healthy tissue of the same type.

29. The device of claim 27 wherein said corresponding force measurement of healthy tissue is assigned a value of ten and said ratio is expressed as an integer from one to ten.

30. A method of determining the response of cartilage to indentation, comprising:
   (a) positioning a testing tip through skin substantially perpendicular to underlying cartilage;
   (b) displacing a portion of the cartilage with the testing tip by applying force against the cartilage with the testing tip; and
   (c) using a computer to detect and measure the response of the cartilage in terms of force exerted against the testing tip by the cartilage at a set displacement.

31. A method of determining the response of cartilage to indentation, comprising:
   (a) positioning a testing tip through skin substantially perpendicular to underlying cartilage;
   (b) displacing a portion of the cartilage with the testing tip by applying force against the cartilage with the testing tip; and
   (c) using a computer to detect and measure the response of the cartilage in terms of displacement of the cartilage at a constant force applied by the testing tip.

32. A method of determining the response of cartilage to indentation, comprising:
   (a) positioning a testing tip through skin substantially perpendicular to underlying cartilage;
   (b) displacing a portion of the cartilage with the testing tip by applying force against the cartilage with the testing tip; and
   (c) using a computer to detect and measure the response of the cartilage and display the results.

33. A method for determining the state of health or disease of cartilage tissue comprising:
   (a) indenting the cartilage to a predetermined displacement using a testing tip and measuring the force required to achieve said displacement;
   (b) using a computer to determine the ratio of said force measurement to at least one corresponding measurement of healthy tissue of the same type, wherein said measurement for healthy tissue is assigned a value of 10;
   (c) displaying said ratio as an integer from one to ten.

34. The method of claim 33 wherein said force measurement is the peak force value multiplied by the time in seconds to reach said peak value.

35. The method of claim 33 wherein said force measurement for healthy tissue is the mean of at least about twelve measurements of healthy tissue of the same type.

* * * * *